US012180489B2

(12) United States Patent
Nuccio et al.

(10) Patent No.: US 12,180,489 B2
(45) Date of Patent: Dec. 31, 2024

(54) MODIFIED EXCISABLE MON87708 SOYBEAN TRANSGENIC HERBICIDE RESISTANCE LOCUS

(71) Applicant: INARI AGRICULTURE TECHNOLOGY, INC., Cambridge, MA (US)

(72) Inventors: Michael Lee Nuccio, Salem, NH (US); Michael Andreas Kock, Rheinfelden (DE); Joshua L. Price, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/058,144

(22) Filed: Nov. 22, 2022

(65) Prior Publication Data

US 2023/0083144 A1 Mar. 16, 2023

Related U.S. Application Data

(63) Continuation of application No. PCT/US2021/043897, filed on Jul. 30, 2021.

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,951, filed on Feb. 4, 2021, provisional application No. 63/199,949, filed on Feb. 4, 2021, provisional application No. 63/199,930, filed on Feb. 3, 2021, provisional application No. 63/059,813, filed on Jul. 31, 2020, provisional application No. 63/059,860, filed on Jul. 31, 2020, provisional application No. 63/059,916, filed on Jul. 31, 2020, provisional application No. 63/059,963, filed on Jul. 31, 2020.

(51) Int. Cl.

| | |
|---|---|
| ***C12N 15/82*** | (2006.01) |
| ***A01H 1/02*** | (2006.01) |
| ***A01H 5/10*** | (2018.01) |
| ***A01H 6/46*** | (2018.01) |
| ***A01H 6/54*** | (2018.01) |
| ***C07K 14/41*** | (2006.01) |
| ***C07K 14/415*** | (2006.01) |
| ***C12N 9/22*** | (2006.01) |
| ***C12N 15/11*** | (2006.01) |
| ***C12Q 1/68*** | (2018.01) |
| ***C12Q 1/6834*** | (2018.01) |
| ***C12Q 1/6895*** | (2018.01) |

(52) U.S. Cl.

CPC .......... *C12N 15/8201* (2013.01); *A01H 1/02* (2013.01); *A01H 5/10* (2013.01); *A01H 6/4684* (2018.05); *A01H 6/542* (2018.05); *C07K 14/415* (2013.01); *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01); *C12Q 2600/156* (2013.01); *C12Q 2600/158* (2013.01)

(58) Field of Classification Search

CPC .......................... A01H 6/542; C12N 15/8213
See application file for complete search history.

(56) References Cited

U.S. PATENT DOCUMENTS

| | | | | |
|---|---|---|---|---|
| 7,632,985 | B2 | 12/2009 | Malven et al. | |
| 8,232,456 | B2 | 7/2012 | Long et al. | |
| 8,450,561 | B2 | 5/2013 | Beazley et al. | |
| 8,455,720 | B2 | 6/2013 | Long et al. | |
| 8,501,407 | B2 * | 8/2013 | Brinker | C12N 9/0071 536/23.6 |
| 8,575,434 | B2 | 11/2013 | Diehn et al. | |
| 8,680,363 | B2 | 3/2014 | Bard et al. | |
| 9,447,428 | B2 | 9/2016 | Brinker et al. | |
| 9,540,655 | B2 | 1/2017 | Cui et al. | |
| 11,041,172 | B2 | 6/2021 | Cermak | |
| 11,214,811 | B1 | 1/2022 | Nuccio et al. | |
| 11,242,534 | B1 | 2/2022 | Nuccio et al. | |
| 11,326,177 | B2 | 5/2022 | Price et al. | |
| 11,359,210 | B2 | 6/2022 | Price et al. | |
| 2003/0088081 | A1 | 5/2003 | Maliga et al. | |

(Continued)

FOREIGN PATENT DOCUMENTS

| | | | | |
|---|---|---|---|---|
| WO | WO-2011091311 A2 * | 7/2011 | | A01H 1/02 |
| WO | 2022026375 A1 | 2/2022 | | |

(Continued)

OTHER PUBLICATIONS

Meriam Webster dictionary (Variant Definition & Meaning—Merriam-Webster). https://www.merriam-webster.com/dictionary/variant, accessed May 23, 2023. (Year: 2023).*

(Continued)

*Primary Examiner* — Cathy Kingdon
*Assistant Examiner* — Santosh Sharma
(74) *Attorney, Agent, or Firm* — McKee, Voorhees & Sease, PLC

(57) ABSTRACT

Transgenic INHT30 soybean plants comprising modifications of the MON87708 soybean locus which provide for facile excision of the modified MON87708 transgenic locus or portions thereof, methods of making such plants, and use of such plants to facilitate breeding are disclosed.

12 Claims, 4 Drawing Sheets

Figure 1:
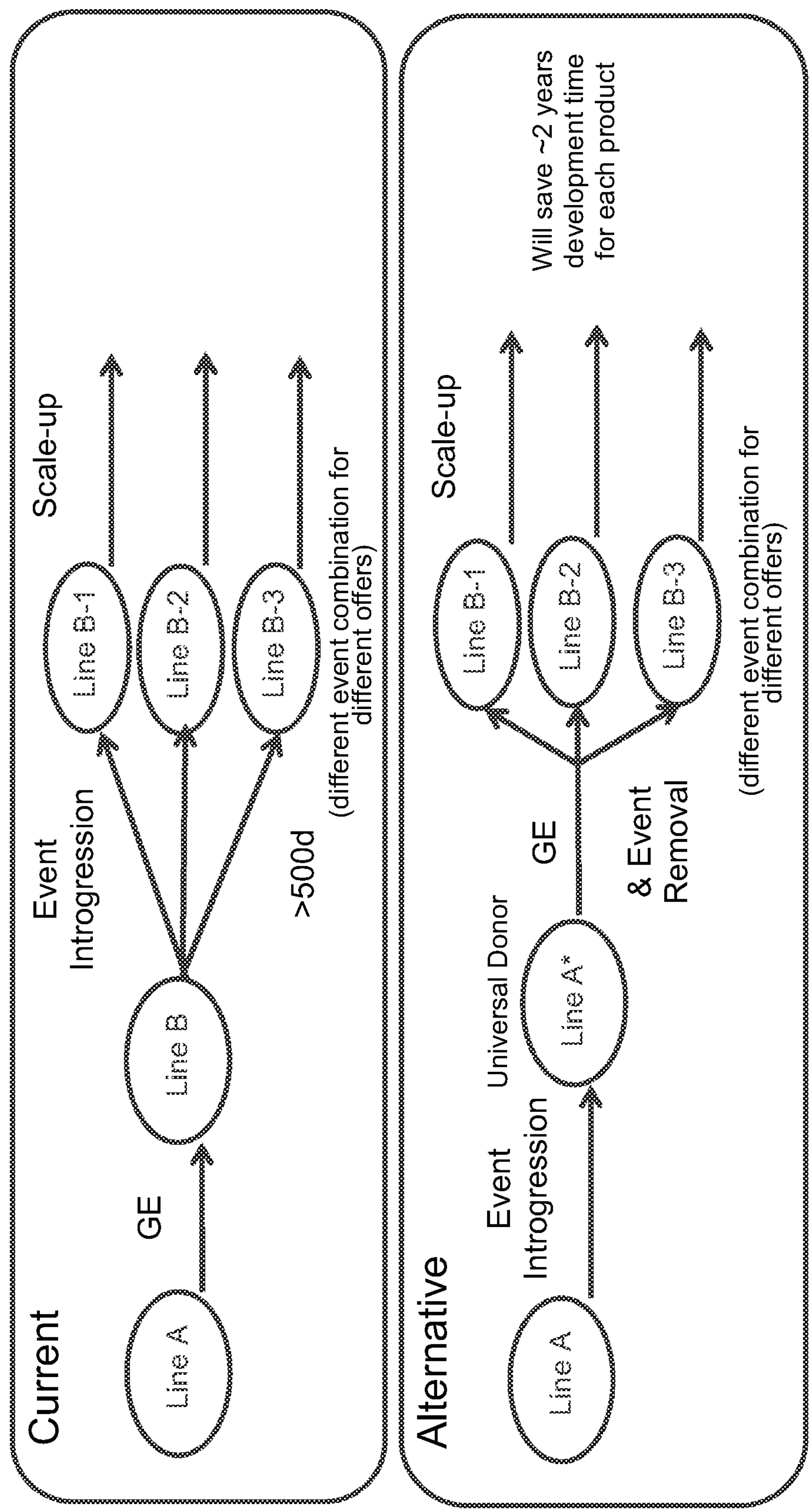

Specification includes a Sequence Listing.

(56) References Cited

U.S. PATENT DOCUMENTS

| | | | |
|---|---|---|---|
| 2010/0162428 | A1 | 6/2010 | Brown et al. |
| 2011/0191899 | A1 | 8/2011 | Ainley et al. |
| 2013/0212747 | A1 | 8/2013 | Cui et al. |
| 2013/0296170 | A1 | 11/2013 | Hanger et al. |
| 2013/0324408 | A1 | 12/2013 | Cui et al. |
| 2014/0041083 | A1 | 2/2014 | Cui et al. |
| 2015/0059010 | A1 | 2/2015 | Cigan et al. |
| 2015/0082478 | A1 | 3/2015 | Cigan et al. |
| 2016/0029631 | A1 | 2/2016 | Hellwege et al. |
| 2016/0333363 | A1 | 11/2016 | Srivastava |
| 2017/0166912 | A1 | 6/2017 | Brower-Toland et al. |
| 2018/0163218 | A1 | 6/2018 | Corbin et al. |
| 2019/0112614 | A1 | 4/2019 | Russell et al. |
| 2019/0136249 | A1 | 5/2019 | Sakai et al. |
| 2019/0284644 | A1 | 9/2019 | Mackenzie et al. |
| 2019/0320607 | A1 | 10/2019 | Christensen et al. |
| 2019/0352655 | A1 | 11/2019 | Niu et al. |
| 2020/0157554 | A1 | 5/2020 | Cigan et al. |
| 2020/0208172 | A1 | 7/2020 | Ikeda et al. |
| 2020/0399626 | A1 | 12/2020 | Liu et al. |
| 2020/0405649 | A1 | 12/2020 | Wang et al. |
| 2022/0030806 | A1 | 2/2022 | Price et al. |
| 2022/0030822 | A1 | 2/2022 | Nuccio et al. |
| 2022/0033833 | A1 | 2/2022 | Gilbertson et al. |
| 2022/0033836 | A1 | 2/2022 | Price et al. |
| 2022/0098602 | A1 | 3/2022 | Nuccio et al. |
| 2022/0154194 | A1 | 5/2022 | Nuccio et al. |
| 2022/0251584 | A1 | 8/2022 | Nuccio et al. |
| 2022/0364105 | A1 | 11/2022 | Price et al. |
| 2023/0077473 | A1 | 3/2023 | Price et al. |
| 2023/0078387 | A1 | 3/2023 | Kock et al. |
| 2023/0083144 | A1 | 3/2023 | Nuccio et al. |
| 2023/0087222 | A1 | 3/2023 | Kock et al. |
| 2023/0147013 | A1 | 5/2023 | Nuccio et al. |
| 2023/0203514 | A1 | 6/2023 | Price et al. |
| 2023/0265445 | A1 | 8/2023 | Kock et al. |
| 2024/0011042 | A1 | 1/2024 | Kock et al. |

FOREIGN PATENT DOCUMENTS

| | | | |
|---|---|---|---|
| WO | 2022026379 | A1 | 2/2022 |
| WO | 2022026390 | A1 | 2/2022 |
| WO | 2022026395 | A2 | 2/2022 |
| WO | 2022026403 | A2 | 2/2022 |
| WO | 2022026540 | A1 | 2/2022 |
| WO | 2022026801 | A1 | 2/2022 |

OTHER PUBLICATIONS

Zhang et al., 2015, Off-target effects in CRISPR/Cas9-mediated genome engineering. Molecular Therapy-Nucleic Acids, 4, e264. ( Year: 2015).*

Zhong et al., 2018, Plant genome editing using FnCpf1 and LbCpf1 nucleases at redefined and altered PAM sites. Molecular plant, 11(7), 999-1002. (Year: 2018).*

Li et al., 2018, Expanding the scope of CRISPR/Cpf1-mediated genome editing in rice. Molecular Plant, 11(7), 995-998. (Year: 2018).*

Bagemann et al., 2017, Precise insertion and guided editing of higher plant genomes using Cpf1 CRISPR nucleases. Scientific reports, 7(1), 11606. (Year: 2017).*

Bagemann et al., 2017, Precise insertion and guided editing of higher plant genomes using Cpf1 CRISPR nucleases (Supplementary Data). Scientific reports, 7(1), 11606. (Year: 2017).*

Zhong et al., 2018, Plant genome editing using FnCpf1 and LbCpf1 nucleases at redefined and altered PAM sites (Supplementary Data). Molecular plant, 11(7), 999-1002. (Year: 2018).*

Finnigan et al., 2016; mCAL: a new approach for versatile multiplex action of Cas9 using one sgRNA and loci flanked by a programmed target sequence. G3: Genes, Genomes, Genetics, 6(7), 2147-2156 (reference Publication, see IDS). (Year: 2016).*

Toth et al., 2020, Improved LbCas 12a variants with altered PAM specificities further broaden the genome targeting range of Cas12a nucleases. Nucleic acids research, 48(7), 3722-3733 (Year: 2020).*

Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.

Biopesticides Registration Action Document, "Bacillus thuringiensis Vip3Aa20 Insecticidal Protein and the Genetic Material Necessary for Its Production (via Elements of Vector pNOV1300) in Event MIR 162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.

Bissler, J.J., "Triplex DNA and human disease," Frontiers in Bioscience, May 1, 2007, vol. 12, pp. 4536-4546.

Bortesi et al., "The CRISPR/Cas9 system for plant genome editing and beyond," Biotechnology Advances, Dec. 20, 2014, vol. 33, Issue 1, pp. 41-52.

Charpentier et al., "Biogenesis pathways of RNA guides in archaeal and bacterial CRISPR-Cas adaptive immunity," FEMS Microbiology Reviews, May 19, 2015, vol. 39, Issue 3, pp. 428-441.

Cho et al., "Nonallelic homologous recombination events responsible for copy number variation within an RNA silencing locus," Plant Direct, vol. 3, Aug. 27, 2019, 16 pages.

Du et al., "Construction of Marker-Free Genetically Modified Maize Using a Heat-Inducible Auto-Excision Vector," Genes, May 17, 2019, vol. 10, No. 374, 17 pages.

Du et al., "Infection of Embryonic Callus with Agrobacterium Enables High-Speed Transformation of Maize," International Journal of Molecular Sciences, Jan. 11, 2019, vol. 20, No. 279, 15 pages.

Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.

Gurusaran et al., "RepEx: Repeat extractor for biological sequences," Genomics, Jul. 21, 2013, vol. 102, pp. 403-408.

International Searching Authority in connection with PCT/US21/43897 filed Jul. 30, 2021, "Invitation to Pay Additional Fees And, Where Applicable, Protest Fee," mailed Oct. 27, 2021, 3 pages.

International Searching Authority in connection with PCT/US21/43935 filed Jul. 30, 2021, "Invitation to Pay Additional Fees And, Where Applicable, Protest Fee," mailed Oct. 26, 2021, 3 pages.

International Searching Authority in connection with PCT/US21/43945 filed Jul. 30, 2021, "Invitation to Pay Additional Fees And, Where Applicable, Protest Fee," mailed Oct. 27, 2021, 3 pages.

Kim et al., "CRISPR/Cpf1-mediated DNA-free plant genome editing," Nature Communications, Feb. 16, 2017, vol. 8, Article No. 14406, 7 pages.

Li et al., "Expanding the Scope of CRISPR/Cpf1-Mediated Genome Editing in Rice," Molecular Plant, Jul. 2, 2018, vol. 11, No. 7, pp. 995-998, 14 pages.

Luo et al., "Improperly Terminated, Unpolyadenylated mRNA of Sense Transgenes is Targeted by RDR6-Mediated RNA Silencing in *Arabidopsis*," The Plant Cell, Mar. 23, 2007, vol. 19, pp. 943-958.

Malzahn et al., "Application of CRISPR-Casl 2a temperature sensitivity for improved genome editing in rice, maize, and *Arabidopsis*," BMC Biology, Jan. 31, 2019, vol. 17, No. 9, 14 pages.

Non-Final Office Action in U.S. Appl. No. 17/248,936, mailed Mar. 25, 2021, 25 pages.

Non-Final Office Action in U.S. Appl. No. 17/249,640, mailed Jun. 29, 2021, 10 pages.

Non-Final Office Action in U.S. Appl. No. 17/302,110, mailed Jun. 29, 2021, 22 pages.

Non-Final Office Action in U.S. Appl. No. 17/302,121, mailed Jul. 8, 2021, 10 pages.

Non-Final Office Action in U.S. Appl. No. 17/302,739, mailed Aug. 3, 2021, 24 pages.

Notice of Allowance in U.S. Appl. No. 17/249,640, mailed Sep. 22, 2021, 7 pages.

Que et al., "Maize transformation technology development for commercial event generation," Frontiers in Plant Science, Aug. 5, 2014, vol. 5, Article No. 379, 19 pages.

(56) References Cited

OTHER PUBLICATIONS

Srivastava et al., "Gene Stacking by recombinases," Plant Biotechnology Journal, Feb. 2016, vol. 14, pp. 471-482.
Srivastava, et al., "Dual-targeting by CRISPR/Cas9 for precise excision of transgenes from rice genome," Plant Cell Tissue and Organ Culture, Jan. 20, 2017, vol. 129, pp. 153-160.
Ward et al., "Petition for Determination of Nonregulated Status for Insect-Resistant MIR162 Maize," Syngenta Biotechnology, Inc., Aug. 31, 2007, 271 pages.
"What is a CRISPR-Cas system?," CRISPR-CAS++, Universite Paris-Saclay, accessed Nov. 2, 2021. Retrieved from the Internet <URL:https://crisprcas.i2bc.paris-saclay.fr/Home/About>, 2 pages.
Xing et al., "Revealing frequent alternative polyadenylation and widespread low-level transcription read-through of hovel plant transcription terminators," Plant Biotechnology Journal, Sep. 2010, vol. 8, pp. 772-782.
Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.
Danilo et al., "The DFR locus: A smart landing pad for targeted transgene insertion in tomato," PLoS One, Dec. 6, 2018, vol. 13, No. 12, pp. 1-14.
Gleditzsch et al., "PAM identification by CRISPR-Cas effector complexes: diversified mechanisms and structures," RNA Biology, 2019, vol. 16, No. 4, pp. 504-517.
International Search Report in PCT/US2021/043161, mailed Jan. 5, 2022, 6 pages.
International Search Report in PCT/US2021/043170, mailed Jan. 5, 2022, 6 pages.
International Search Report in PCT/US2021/043187, mailed Jan. 6, 2022, 6 pages.
International Search Report in PCT/US2021/043192, mailed Jan. 27, 2022, 7 pages.
International Search Report in PCT/US2021/043207, mailed Jan. 27, 2022, 6 pages.
International Search Report in PCT/US2021/043440, mailed Dec. 2, 2021, 3 pages.
International Search Report in PCT/US2021/043468, mailed Nov. 26, 2021, 4 pages.
International Search Report in PCT/US2021/043479, mailed Nov. 23, 2021, 3 pages.
International Search Report in PCT/US2021/043483, mailed Dec. 16, 2021, 3 pages.
International Search Report in PCT/US2021/043496, mailed Dec. 1, 2021, 4 pages.
International Search Report in PCT/US2021/043851, mailed Dec. 30, 2021, 6 pages.
International Search Report in PCT/US2021/043919, mailed Jan. 20, 2022, 8 pages.
International Search Report in PCT/US2021/043933, mailed Dec. 30, 2021, 6 pages.
International Search Report in PCT/US2021/044198, mailed Jan. 19, 2022, 6 pages.
Non-Final Office Action in U.S. Appl. No. 17/302,110, mailed May 24, 2023, 27 pages.
Non-Final Office Action in U.S. Appl. No. 17/650,031, mailed May 26, 2023, 11 pages.
Non-Final Office Action in U.S. Appl. No. 17/680,647, mailed Jun. 23, 2023, 11 pages.
Non-Final Office Action in U.S. Appl. No. 18/057,860, mailed Jun. 1, 2023, 49 pages.
Non-Final Office Action in U.S. Appl. No. 18/057,867, mailed Jun. 7, 2023, 17 pages.
Non-Final Office Action in U.S. Appl. No. 18/058,081, mailed Apr. 11, 2023, 19 pages.
Non-Final Office Action in U.S. Appl. No. 18/058,156, mailed May 19, 2023, 24 pages.
Non-Final Office Action in U.S. Appl. No. 18/058,161, mailed Apr. 11, 2023, 15 pages.
Non-Final Office Action in U.S. Appl. No. 18/162,134, mailed Jun. 21, 2023, 28 pages.
Notice of Allowance in U.S. Appl. No. 17/248,936, mailed Mar. 10, 2022, 7 pages.
Notice of Allowance in U.S. Appl. No. 17/302,121, mailed Nov. 15, 2021, 7 pages.
Notice of Allowance in U.S. Appl. No. 17/302,739, mailed Mar. 30, 2022, 7 pages.
Notice of Allowance in U.S. Appl. No. 17/680,647, mailed Apr. 27, 2023, 7 pages.
Shi et al., "ARGOS8 variants generated by CRISPR-Cas9 improve maize grain yield under field drought stress conditions," Plant Biotechnology Journal, 2017, vol. 15, pp. 207-216.
Yau et al., "Less is more: strategies to remove marker genes from transgenic plants," BMC Biotechnology, 2013, vol. 13, No. 36, pp. 1-23.
Non-Final Office Action in U.S. Appl. No. 17/680,647, mailed Jun. 23, 2022, 11 pages.
GenBank Accession No. CP0049894, "Arachis ipaensis cultivar K30076 chromosome 03," Jun. 3, 2020, https://www.ncbi.nlm.nih.gov/nuccore/CP049894, 2 pages.
International Search Report and Written Opinion in PCT/US2021/043897, mailed Feb. 10, 2022, 12 pages.
International Search Report and Written Opinion in PCT/US2021/043935, mailed Jan. 6, 2022, 13 pages.
International Search Report and Written Opinion in PCT/US2021/043945, mailed Jan. 21, 2022, 15 pages.
Li et al. Expanding the scope of CRISPR/Cpf1-mediated genome editing in rice; Molecular Plant 11:995-998, 2018, Supplemental Data, p. 1-10.
Ali et al., "Fusion of the Cas9 endonuclease and the VirD2 relaxase facilitates homology-directed repair for precise genome engineering in rice," Communications Biology, vol. 3, Jan. 2020, 13 pages.
Bernabe-Orts et al., "Assessment of Cas12a-mediated gene editing efficiency in plants," Plant Biotechnology Journal, vol. 17, No. 10, 2019, pp. 1971-1984.
Cai et al., "Broadening the targetable space: engineering and discovery of PAM-flexible Cas proteins," Trends in Microbiology, May 2024, 4 pages.
Non-Final Office Action in U.S. Appl. No. 17/302,110, mailed Oct. 16, 2024, 24 pages.
Extended European Search Report in EP21849192.6, mailed Aug. 30, 2024, 17 pages.
Lee et al., "Activities and specificities of CRISPR/Cas9 and Cas12a nucleases for targeted mutagenesis in maize," Plant Biotechnology Journal, vol. 17, No. 2, 2019, pp. 362-372.
Non-Final Office Action in U.S. Appl. No. 18/162,134, mailed Sep. 26, 2024, 27 pages.
Wang et al., "Generation of marker-free transgenic rice using CRISPR/Cas9 system controlled by floral specific promoters," Journal of Genetics and Genomics, vol. 46, 2019, pp. 61-64.

* cited by examiner

SEQUENCE LISTING

```
Sequence total quantity: 27
SEQ ID NO: 1            moltype = DNA  length = 5946
FEATURE                 Location/Qualifiers
source                  1..5946
                        mol_type = other DNA
                        organism = synthetic construct
SEQUENCE: 1
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata tttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcaccttcaa acactgatag  1140
tttaaactga aggcgggaaa cgacaatctg atccccatca agctagcttc tgcaggtcct  1200
gctcgagcgg ccgcagatct tgagccaatc aaagaggagt gatgtagacc taaagcaata  1260
atggagccat gacgtaaggg cttacgccca tacgaaataa ttaaaggctg atgtgacctg  1320
tcggtctctc agaaccttta ctttttatgt ttggcgtgta tttttaaatt tccacggcaa  1380
tgacgatgtg acccaacgag atcttgagcc aatcaaagag gagtgatgta gacctaaagc  1440
aataatggag ccatgacgta agggcttacg cccatacgaa ataattaaag gctgatgtga  1500
cctgtcggtc tctcagaacc tttacttttt atatttggcg tgtattttta aatttccacg  1560
gcaatgacga tgtgacctgt gcatccgctt tgcctataaa taagttttag tttgtattga  1620
tcgacacggt cgagaagaca cggccataag cttggatcct cgagaattct caacacaaca  1680
tatacaaaac aaacgaatct caagcaatca agcattctac ttctattgca gcaatttaaa  1740
tcatttcttt taaagcaaaa gcaattttct gaaaatttc accatttacg aacgatagcc  1800
atggcttcta tgatatcctc ttccgctgtg acaacagtca gccgtgcctc tagggggcaa  1860
tccgccgcaa tggctccatt cggcggcctc aaatccatga ctggattccc agtgaggaag  1920
gtcaacactg acattacttc cattacaagc aatggtggaa gagtaaagtg catgcaggtg  1980
tggcctccaa ttggaaagaa gaagtttgag actctttcct atttgccacc attgacgaga  2040
gattcccggg ccatggccac cttcgtccgc aatgcctggt atgtggcggc gctgcccgag  2100
gaactgtccg aaaagccgct cggccggacg attctcgaca caccgctcgc gctctaccgc  2160
cagcccgacg gtgtggtcgc ggcgctgctc gacatctgtc cgcaccgctt cgcgccgctg  2220
```

```
agcgacggca tcctcgtcaa cggccatctc caatgcccct atcacgggct ggaattcgat  2280
ggcggcgggc agtgcgtcca taacccgcac ggcaatggcg cccgcccggc ttcgctcaac  2340
gtccgctcct tcccggtggt ggagcgcgac gcgctgatct ggatctgtcc cggcgatccg  2400
gcgctggccg atcctggggc gatccccgac ttcggctgcc gcgtcgatcc cgcctatcgg  2460
accgtcggcg gctatgggca tgtcgactgc aactacaagc tgctggtcga caacctgatg  2520
gacctcggcc acgcccaata tgtccatcgc gccaacgccc agaccgacgc cttcgaccgg  2580
ctggagcgcg aggtgatcgt cggcgacggt gagatacagg cgctgatgaa gattcccggc  2640
ggcacgccga gcgtgctgat ggccaagttc ctgcgcggcg ccaataccccc cgtcgacgct  2700
tggaacgaca tccgctggaa caaggtgagc gcgatgctca acttcatcgc ggtggcgccg  2760
gaaggcaccc cgaaggagca gagcatccac tcgcgcggta cccatatcct gaccccgag  2820
acggaggcga gctgccatta tttcttcggc tcctcgcgca atttcggcat cgacgatccg  2880
gagatggacg gcgtgctgcg cagctggcag gctcaggcgc tggtcaagga ggacaaggtc  2940
gtcgtcgagg cgatcgagcg ccgccgcgcc tatgtcgagg cgaatggcat ccgcccggcg  3000
atgctgtcgt gcgacgaagc cgcagtccgt gtcagccgcg agatcgagaa gcttgagcag  3060
ctcgaagccg cctgaaccgg cttatgctgc acgggcgggg cggggcggtt tcgatcggct  3120
cgcctgtccc ggcgatattc tagagctttc gttcgtatca tcggtttcga caacgttcgt  3180
caagttcaat gcatcagttt cattgcgcac acaccagaat cctactgagt ttgagtatta  3240
tggcattggg aaaactgttt ttcttgtacc atttgttgtg cttgtaattt actgtgtttt  3300
ttattcggtt ttcgctatcg aactgtgaaa tggaaatgga tggagaagag ttaatgaatg  3360
atatggtcct tttgttcatt ctcaaattaa tattatttgt tttttctctt atttgttgtg  3420
tgttgaattt gaaattataa gagatatgca aacattttgt tttgagtaaa aatgtgtcaa  3480
atcgtggcct ctaatgaccg aagttaatat gaggagtaaa acacttgtag ttgtaccatt  3540
atgcttattc actaggcaac aaatatattt tcagacctag aaaagctgca aatgttactg  3600
aatacaagta tgtcctcttg tgttttagac atttatgaac tttcctttat gtaattttcc  3660
agaatccttg tcagattcta atcattgctt tataattata gttatactca tggatttgta  3720
gttgagtatg aaaatatttt ttaatgcatt ttatgacttg ccaattgatt gacaacatgc  3780
atcaatcgcg gccgctctag aactagtgga tcccccctt taagggggct gcaggaattc  3840
gatatcaagc tttggcgcgc caaatcgtga agtttctcat ctaagccccc atttggacgt  3900
gaatgtagac acgtcgaaat aaagatttcc gaattagaat aatttgttta ttgctttcgc  3960
ctataaatac gacggatcgt aatttgtcgt tttatcaaaa tgtactttca ttttataata  4020
acgctgcgga catctacatt tttgaattga aaaaaaattg gtaattactc tttcttttc  4080
tccatattga ccatcatact cattgctgat ccatgtagat ttcccggact ttagctcaaa  4140
atgcatgtat ttattagcgt tctgtctttt cgttaatttg ttctcatcat aatattgtga  4200
caaaaatata gctaggaaag ctttccatgc atattttgta agcaatgaag tatatagtgg  4260
atgcaatgtc tctatatatt cactagtcga gaaaattgcg gacagttctg agattgattg  4320
gcttcatggc cctacggtgc atctattacc attgtctttg catttgtcat acaaaaaggt  4380
ggaccatatt catgttatgt aaaaacaaac aaaatcacgc agtgcacatc ttctgcagaa  4440
tgtgtaggtt aaccttatta cacttgatta agttaagtgt catgccatta gtttgagatt  4500
gaacttaaaa tctttaatca agatcttaga tatggaaaaa attgtaattc cattaaagat  4560
aataagattt ttggatagaa attaattatc aattttacat taataacata ataatttgaa  4620
gaaaaaaagt aagggtcata atcatactaa ccagagtaat ttgacacgtg aaggggacac  4680
tatgaaagca aattactttt ggttcctaaa ggttaggcaa gggaaagaaa gaatttgcac  4740
ttaattagca ctattttcaa aattattatg tttcttttcc ttatcttgct taaaatttgc  4800
ttattgtgtt attattatta ttattgttat gcatgatcaa ttattcatca aagatcgatc  4860
tccaacctgc caggaaatcc gctgatttgt ttgcttccaa tgtgagagat ccaagatcag  4920
aattctggaa ggtagtgctg actaccaagg tagcaaaata atgatattgg ggaaggtgaa  4980
aaatatgtag tactagtact tctactacaa aatttcaaaa agggttttgt gatttgtgca  5040
taagaatctt tttgcatttg tctgtaagct tgaaaattac acgtggcaca agtcacttgc  5100
agccaaagaa cctttctgtg accaattatg ttccctgagc tgaatagtgg ttcttattct  5160
aatctcatca atatctaatt acctagtgaa tatactacta gactattgca gtgttattaa  5220
tatcttaatg atagactatt gcagcagaca gaaattacag gtattattat atactaatat  5280
acaattctgc attttccaca cttttcccct gcccatgctt ccatgccact gaagtctgaa  5340
accacattgg cagattttgc tatctagaaa ttaaataaca atataagttt gtatatttat  5400
atttcatatt tttttagtac attttatttt tgcacactct ataattccat gattccttga  5460
ttatcggaga atgatgtgat atgcaaacca cgagttagaa ccatcaaatc aagcaaagat  5520
atggatggaa tgcctttaat ggaaagatta attcaaaggg gcagaaactg gtaatttttt  5580
cttcaactga atgctatgca gtatgcagca gatctttcat ttacagaata tctgcaaaac  5640
cttgtgttgg agatcttacc tattgaataa tgatataggt aaaataaagt atttaatttc  5700
accataactt ttaagatgat gttaaaatga tctatgcaat tcatgttgga tcgaatatta  5760
aagatgtcac atctaatgat actatgataa aaataaagta taatttctga tcttataagt  5820
caaaataaat catgtaaata taaattaatt ctcttcttat aaattaattt tatataatta  5880
agatagatcc aatgtgaact ctaagaccat gcatatataa aaatcattat caagtgaata  5940
tgcaac                                                             5946
```

```
SEQ ID NO: 2          moltype = DNA  length = 5939
FEATURE               Location/Qualifiers
source                1..5939
                      mol_type = other DNA
                      organism = synthetic construct
SEQUENCE: 2
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
```

-continued

```
aaaatctgac atagtatatg tttagattaa aatttgtaaa tgtaagtttg aattaaaaaa  600
gtatattata aacttgagtt tggtataaata tttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcaccttcaa acgtttaaac  1140
tgaaggcggg aaacgacaat ctgatcccca tcaagctagc ttctgcaggt cctgctcgag  1200
cggccgcaga tcttgagcca atcaaagagg agtgatgtag acctaaagca ataatggagc  1260
catgacgtaa gggcttacgc ccatacgaaa taattaaagg ctgatgtgac ctgtcggtct  1320
ctcagaacct ttacttttta tgtttggcgt gtatttttaa atttccacgg caatgacgat  1380
gtgacccaac gagatcttga gccaatcaaa gaggagtgat gtagacctaa agcaataatg  1440
gagccatgac gtaagggctt acgcccatac gaaataatta aaggctgatg tgacctgtcg  1500
gtctctcaga acctttactt tttatatttg gcgtgtattt ttaaatttcc acggcaatga  1560
cgatgtgacc tgtgcatccg ctttgcctat aaataagttt tagtttgtat tgatcgacac  1620
ggtcgagaag acacggccat aagcttggat cctcgagaat tctcaacaca acatatacaa  1680
aacaaacgaa tctcaagcaa tcaagcattc tacttctatt gcagcaattt aaatcatttc  1740
ttttaaagca aaagcaattt tctgaaaatt ttcaccattt acgaacgata gccatggctt  1800
ctatgatatc ctcttccgct gtgacaacag tcagccgtgc ctctaggggg caatccgccg  1860
caatggctcc attcggcggc ctcaaatcca tgactggatt cccagtgagg aaggtcaaca  1920
ctgacattac ttccattaca agcaatggtg gaagagtaaa gtgcatgcag gtgtggcctc  1980
caattggaaa gaagaagttt gagactcttt cctatttgcc accattgacg agagattccc  2040
gggccatggc caccttcgtc cgcaatgcct ggtatgtggc ggcgctgccc gaggaactgt  2100
ccgaaaagcc gctcggccgg acgattctcg acacaccgct cgcgctctac cgccagcccg  2160
acggtgtggt cgcggcgctg ctcgacatct gtccgcaccg cttcgcgccg ctgagcgacg  2220
gcatcctcgt caacggccat ctccaatgcc cctatcacgg gctggaattc gatggcggcg  2280
ggcagtgcgt ccataacccg cacggcaatg gcgcccgccc ggcttcgctc aacgtccgct  2340
ccttcccggt ggtggagcgc gacgcgctga tctggatctg tcccggcgat ccggcgctgg  2400
ccgatcctgg ggcgatcccc gacttcggct gccgcgtcga tcccgcctat cggaccgtcg  2460
gcggctatgg gcatgtcgac tgcaactaca agctgctggt cgacaacctg atggacctcg  2520
gccacgccca atatgtccat cgcgccaacg cccagaccga cgccttcgac cggctggagc  2580
gcgaggtgat cgtcggcgac ggtgagatac aggcgctgat gaagattccc ggcggcacgc  2640
cgagcgtgct gatggccaag ttcctgcgcg gcgccaatac ccccgtcgac gcttggaacg  2700
acatccgctg gaacaaggtg agcgcgatgc tcaacttcat cgcggtggcg ccggaaggca  2760
ccccgaagga gcagagcatc cactcgcgcg gtacccatat cctgaccccc gagacggagg  2820
cgagctgcca ttatttcttc ggctcctcgc gcaatttcgg catcgacgat ccggagatgg  2880
acggcgtgct gcgcagctgg caggctcagg cgctggtcaa ggaggacaag gtcgtcgtcg  2940
aggcgatcga gcgccgccgc gcctatgtcg aggcgaatgg catccgcccg gcgatgctgt  3000
cgtgcgacga agccgcagtc cgtgtcagcc gcgagatcga gaagcttgag cagctcgaag  3060
ccgcctgaac cggcttatgc tgcacgggcg gggcggggcg gtttcgatcg gctcgcctgt  3120
cccggcgata ttctagagct ttcgttcgta tcatcggttt cgacaacgtt cgtcaagttc  3180
aatgcatcag tttcattgcg cacacaccag aatcctactg agtttgagta ttatggcatt  3240
gggaaaactg tttttcttgt accatttgtt gtgcttgtaa tttactgtgt tttttattcg  3300
gttttcgcta tcgaactgtg aaatggaaat ggatggagaa gagttaatga atgatatggt  3360
ccttttgttc attctcaaat taatattatt tgttttttct cttatttgtt gtgtgttgaa  3420
tttgaaatta taagagatat gcaaacattt tgttttgagt aaaaatgtgt caaatcgtgg  3480
cctctaatga ccgaagttaa tatgaggagt aaaacacttg tagttgtacc attatgctta  3540
ttcactaggc aacaaatata ttttcagacc tagaaaagct gcaaatgtta ctgaatacaa  3600
gtatgtcctc ttgtgtttta gacatttatg aactttcctt tatgtaattt tccagaatcc  3660
ttgtcagatt ctaatcattg ctttataatt atagttatac tcatggattt gtagttgagt  3720
atgaaaatat tttttaatgc attttatgac ttgccaattg attgacaaca tgcatcaatc  3780
gcggccgctc tagaactagt ggatcccccc ctttaagggg gctgcaggaa ttcgatatca  3840
agctttggcg cgccaaatcg tgaagtttct catctaagcc cccatttgga cgtgaatgta  3900
gacacgtcga aataaagatt tccgaattag aataatttgt ttattgcttt cgcctataaa  3960
tacgacggat cgtaatttgt cgttttatca aaatgtactt tcattttata ataacgctgc  4020
ggacatctac atttttgaat tgaaaaaaaa ttggtaatta ctctttcttt ttctccatat  4080
tgaccatcat actcattgct gatccatgta gatttcccgg actttagctc aaaatgcatg  4140
tatttattag cgttctgtct tttcgttaat ttgttctcat cataatattg tgacaaaaat  4200
atagctagga aagctttcca tgcatatttt gtaagcaatg aagtatatag tggatgcaat  4260
gtctctatat attcactagt cgagaaaatt gcggacagtt ctgagattga ttggcttcat  4320
ggccctacgg tgcatctatt accattgtct ttgcatttgt catacaaaaa ggtggaccat  4380
attcatgtta tgtaaaaaca aacaaaatca cgcagtgcac atcttctgca gaatgtgtag  4440
gttaacctta ttacacttga ttaagttaag tgtcatgcca ttagtttgag attgaactta  4500
aaatctttaa tcaagatctt agatatggaa aaaattgtaa ttccattaaa gataataaga  4560
tttttggata gaaattaatt atcaatttta cattaataac ataataattt gaagaaaaaa  4620
agtaagggtc ataatcatac taaccagagt aatttgacac gtgaagggga cactatgaaa  4680
gcaaattact tttggttcct aaaggttagg caagggaaag aaagaatttg cacttaatta  4740
gcactatttt caaaattatt atgtttcttt tccttatctt gcttaaaatt tgcttattgt  4800
gttattatta ttattattgt tatgcatgat caattattca tcaaagatcg atctccaacc  4860
tgccaggaaa tccgctgatt tgtttgcttc caatgtgaga gatccaagat cagaattctg  4920
gaaggtagtg ctgactacca aggtagcaaa ataatgatat tggggaaggt gaaaaatatg  4980
tagtactagt acttctacta caaaatttca aaaagggttt tgtgatttgt gcataagaat  5040
ctttttgcat ttgtctgtaa gcttgaaaat tacacgtggc acaagtcact tgcagccaaa  5100
gaacctttct gtgaccaatt atgttccctg agctgaatag tggttcttat tctaatctca  5160
tcaatatcta attacctagt gaatatacta ctagactatt gcagtgttat taatatctta  5220
atgatagact attgcagcag acagaaatta caggtattat tatatactaa tatacaattc  5280
```

```
tgcattttcc acacttttcc cctgcccatg cttccatgcc actgaagtct gaaaccacat  5340
tggcagattt tgctatctag aaattaaata acaatataag tttgtatatt tatatttcat  5400
atttttttag tacattttta ttttgcacac tctataattc catgattcct tgattatcgg  5460
agaatgatgt gatatgcaaa ccacgagtta gaaccatcaa atcaagcaaa gatatggatg  5520
gaatgccttt aatggaaaga ttaattcaaa ggggcagaaa ctggtaattt tttcttcaac  5580
tgaatgctat gcagtatgca gcagatcttt catttacaga atatctgcaa aaccttgtgt  5640
tggagatctt acctattgaa taatgatata ggtaaaataa agtatttaat ttcaccataa  5700
cttttaagat gatgttaaaa tgatctatgc aattcatgtt ggatcgaata ttaaagatgt  5760
cacatctaat gatactatga taaaaataaa gtataatttc tgatcttata agtcaaaata  5820
aatcatgtaa atataaatta attctcttct tataaattaa ttttatataa ttaagataga  5880
tccaatgtga actctaagac catgcatata taaaaatcat tatcaagtga atatgcaac   5939

SEQ ID NO: 3            moltype = DNA  length = 5966
FEATURE                 Location/Qualifiers
source                  1..5966
                        mol_type = other DNA
                        organism = synthetic construct
SEQUENCE: 3
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcaccttcaa actttagctc  1140
aaaatgcatg tatttattag tttaaactga aggcgggaaa cgacaatctg atccccatca  1200
agctagcttc tgcaggtcct gctcgagcgg ccgcagatct tgagccaatc aaagaggagt  1260
gatgtagacc taaagcaata atggagccat gacgtaaggg cttacgccca tacgaaataa  1320
ttaaaggctg atgtgacctg tcggtctctc agaaccttta ctttttatgt ttggcgtgta  1380
tttttaaatt tccacggcaa tgacgatgtg acccaacgag atcttgagcc aatcaaagag  1440
gagtgatgta gacctaaagc aataatggag ccatgacgta agggcttacg cccatacgaa  1500
ataattaaag gctgatgtga cctgtcggtc tctcagaacc tttacttttt atatttggcg  1560
tgtattttta aatttccacg gcaatgacga tgtgacctgt gcatccgctt tgcctataaa  1620
taagttttag tttgtattga tcgacacggt cgagaagaca cggccataag cttggatcct  1680
cgagaattct caacacaaca tatacaaaac aaacgaatct caagcaatca agcattctac  1740
ttctattgca gcaatttaaa tcatttcttt taaagcaaaa gcaattttct gaaaattttc  1800
accatttacg aacgatagcc atggcttcta tgatatcctc ttccgctgtg acaacagtca  1860
gccgtgcctc tagggggcaa tccgccgcaa tggctccatt cggcggcctc aaatccatga  1920
ctggattccc agtgaggaag gtcaacactg acattacttc cattacaagc aatggtggaa  1980
gagtaaagtg catgcaggtg tggcctccaa ttggaaagaa gaagtttgag actctttcct  2040
atttgccacc attgacgaga gattcccggg ccatggccac cttcgtccgc aatgcctggt  2100
atgtggcggc gctgcccgag gaactgtccg aaaagccgct cggccggacg attctcgaca  2160
caccgctcgc gctctaccgc cagcccgacg gtgtggtcgc ggcgctgctc gacatctgtc  2220
cgcaccgctt cgcgccgctg agcgacggca tcctcgtcaa cggccatctc caatgcccct  2280
atcacgggct ggaattcgat ggcggcggcc agtgcgtcca taacccgcac ggcaatggcg  2340
cccgcccggc ttcgctcaac gtccgctcct tcccggtggt ggagcgcgac gcgctgatct  2400
ggatctgtcc cggcgatccg gcgctggccg atcctggggc gatccccgac ttcggctgcc  2460
gcgtcgatcc cgcctatcgg accgtcggcg gctatgggca tgtcgactgc aactacaagc  2520
tgctggtcga caacctgatg gacctcggcc acgcccaata tgtccatcgc gccaacgccc  2580
agaccgacgc cttcgaccgg ctggagcgcg aggtgatcgt cggcgacggt gagatacagg  2640
cgctgatgaa gattcccggc ggcacgccga gcgtgctgat ggccaagttc ctgcgcggcg  2700
ccaatacccc cgtcgacgct tggaacgaca tccgctggaa caaggtgagc gcgatgctca  2760
acttcatcgc ggtggcgccg gaaggcaccc cgaaggagca gagcatccac tcgcgcggta  2820
cccatatcct gacccccgag acggaggcga gctgccatta tttcttcggc tcctcgcgca  2880
atttcggcat cgacgatccg gagatggacg gcgtgctgcg cagctggcag gctcaggcgc  2940
tggtcaagga ggacaaggtc gtcgtcgagg cgatcgagcg ccgccgcgcc tatgtcgagg  3000
cgaatggcat ccgcccggcg atgctgtcgt gcgacgaagc cgcagtccgt gtcagccgcg  3060
agatcgagaa gcttgagcag ctcgaagccg cctgaaccgg cttatgctgc acgggcgggg  3120
cggggcggtt tcgatcggct cgcctgtccc ggcgatattc tagagctttc gttcgtatca  3180
tcggtttcga caacgttcgt caagttcaat gcatcagttt cattgcgcac acaccagaat  3240
cctactgagt ttgagtatta tggcattggg aaaactgttt ttcttgtacc atttgttgtg  3300
cttgtaattt actgtgtttt ttattcggtt ttcgctatcg aactgtgaaa tggaaatgga  3360
tggagaagag ttaatgaatg atatggtcct tttgttcatt ctcaaattaa tattatttgt  3420
tttttctctt atttgttgtg tgttgaattt gaaattataa gagatatgca aacattttgt  3480
tttgagtaaa aatgtgtcaa atcgtggcct ctaatgaccg aagttaatat gaggagtaaa  3540
acacttgtag ttgtaccatt atgcttattc actaggcaac aaatatattt tcagacctag  3600
aaaagctgca aatgttactg aatacaagta tgtcctcttg tgttttagac atttatgaac  3660
```

```
tttcctttat gtaattttcc agaatccttg tcagattcta atcattgctt tataattata  3720
gttatactca tggatttgta gttgagtatg aaaatatttt ttaatgcatt ttatgacttg  3780
ccaattgatt gacaacatgc atcaatcgcg gccgctctag aactagtgga tcccccccctt  3840
taagggggct gcaggaattc gatatcaagc tttggcgcgc caaatcgtga agtttctcat  3900
ctaagccccc atttggacgt gaatgtagac acgtcgaaat aaagatttcc gaattagaat  3960
aatttgttta ttgctttcgc ctataaatac gacggatcgt aatttgtcgt tttatcaaaa  4020
tgtactttca ttttataata acgctgcgga catctacatt tttgaattga aaaaaaattg  4080
gtaattactc tttctttttc tccatattga ccatcatact cattgctgat ccatgtagat  4140
ttcccggact ttagctcaaa atgcatgtat ttattagcgt tctgtctttt cgttaatttg  4200
ttctcatcat aatattgtga caaaaatata gctaggaaag ctttccatgc atattttgta  4260
agcaatgaag tatatagtgg atgcaatgtc tctatatatt cactagtcga gaaaattgcg  4320
gacagttctg agattgattg gcttcatggc cctacggtgc atctattacc attgtctttg  4380
catttgtcat acaaaaaggt ggaccatatt catgttatgt aaaaacaaac aaaatcacgc  4440
agtgcacatc ttctgcagaa tgtgtaggtt aaccttatta cacttgatta agttaagtgt  4500
catgccatta gtttgagatt gaacttaaaa tctttaatca agatcttaga tatggaaaaa  4560
attgtaattc cattaaagat aataagattt ttggatagaa attaattatc aattttacat  4620
taataacata ataatttgaa gaaaaaaagt aagggtcata atcatactaa ccagagtaat  4680
ttgacacgtg aaggggacac tatgaaagca aattactttt ggttcctaaa ggttaggcaa  4740
gggaaagaaa gaatttgcac ttaattagca ctattttcaa aattattatg tttcttttcc  4800
ttatcttgct taaaatttgc ttattgtgtt attattatta ttattgttat gcatgatcaa  4860
ttattcatca aagatcgatc tccaacctgc caggaaatcc gctgatttgt ttgcttccaa  4920
tgtgagagat ccaagatcag aattctggaa ggtagtgctg actaccaagg tagcaaaata  4980
atgatattgg ggaaggtgaa aaatatgtag tactagtact tctactacaa aatttcaaaa  5040
agggttttgt gatttgtgca taagaatctt tttgcatttg tctgtaagct tgaaaattac  5100
acgtggcaca agtcacttgc agccaaagaa cctttctgtg accaattatg ttccctgagc  5160
tgaatagtgg ttcttattct aatctcatca atatctaatt acctagtgaa tatactacta  5220
gactattgca gtgttattaa tatcttaatg atagactatt gcagcagaca gaaattacag  5280
gtattattat atactaatat acaattctgc attttccaca cttttcccct gcccatgctt  5340
ccatgccact gaagtctgaa accacattgg cagattttgc tatctagaaa ttaaataaca  5400
atataagttt gtatatttat atttcatatt tttttagtac atttttattt tgcacactct  5460
ataattccat gattccttga ttatcggaga atgatgtgat atgcaaacca cgagttagaa  5520
ccatcaaatc aagcaaagat atggatggaa tgcctttaat ggaaagatta attcaaaggg  5580
gcagaaactg gtaatttttt cttcaactga atgctatgca gtatgcagca gatctttcat  5640
ttacagaata tctgcaaaac cttgtgttgg agatcttacc tattgaataa tgatataggt  5700
aaaataaagt atttaatttc accataactt ttaagatgat gttaaaatga tctatgcaat  5760
tcatgttgga tcgaatatta aagatgtcac atctaatgat actatgataa aaataaagta  5820
taatttctga tcttataagt caaaataaat catgtaaata taaattaatt ctcttcttat  5880
aaattaattt tatataatta agatagatcc aatgtgaact ctaagaccat gcatatataa  5940
aaatcattat caagtgaata tgcaac                                      5966

SEQ ID NO: 4            moltype = DNA  length = 27
FEATURE                 Location/Qualifiers
source                  1..27
                        mol_type = other DNA
                        organism = synthetic construct
SEQUENCE: 4
tttaaactat cagtgtttga aggtgag                                     27

SEQ ID NO: 5            moltype = DNA  length = 27
FEATURE                 Location/Qualifiers
source                  1..27
                        mol_type = other DNA
                        organism = synthetic construct
SEQUENCE: 5
tttcccgcct tcagtttaaa ctatcag                                     27

SEQ ID NO: 6            moltype = DNA  length = 27
FEATURE                 Location/Qualifiers
source                  1..27
                        mol_type = other DNA
                        organism = synthetic construct
SEQUENCE: 6
tttagtctca ccttcaaaca ctgatag                                     27

SEQ ID NO: 7            moltype = DNA  length = 27
FEATURE                 Location/Qualifiers
source                  1..27
                        mol_type = other DNA
                        organism = synthetic construct
SEQUENCE: 7
tttagctcaa aatgcatgta tttatta                                     27

SEQ ID NO: 8            moltype = DNA  length = 47
FEATURE                 Location/Qualifiers
source                  1..47
                        mol_type = other DNA
                        organism = synthetic construct
SEQUENCE: 8
agccatttag tttagctcaa aatgcatgta tttattattc aaacact               47
```

```
SEQ ID NO: 9            moltype = DNA  length = 47
FEATURE                 Location/Qualifiers
source                  1..47
                        mol_type = other DNA
                        organism = synthetic construct
SEQUENCE: 9
accttcaaac tttagctcaa aatgcatgta tttattagtt taaactg               47

SEQ ID NO: 10           moltype = DNA  length = 47
FEATURE                 Location/Qualifiers
source                  1..47
                        mol_type = other DNA
                        organism = synthetic construct
SEQUENCE: 10
cttcaaacac tttagctcaa aatgcatgta tttattatta aactgaa               47

SEQ ID NO: 11           moltype = DNA  length = 1127
FEATURE                 Location/Qualifiers
source                  1..1127
                        mol_type = other DNA
                        organism = synthetic construct
SEQUENCE: 11
taagtttgaa ttaaaaaagt atattataaa cttgagtttg gtataatatt ttttatcatc  60
agactttggt ataatatgag ttgatctaaa agtaagttga aggataccaa agggtaatct  120
aaacatgcat gagaaatgtt ggggaatatc tttagtgtaa acaaaaagcc ttataaatta  180
tcatgtcata ctatatatga caaatgttgg tttttgtaat aatcatttta aatatgaaca  240
acaggatttt ctttttaccg tcaaaatatg aataaaagtt aaactcttaa attattgatc  300
ataggtttgc aatttttttt tatagagagg tttgcaattt ctgagttctc aataactgat  360
gattaaatgc gcatcgtttg catgcatgaa aataaattta agaggtaaca tttgaagtct  420
caccttcatg tccggggctg ccaggaaagc ttagatctcc atgagcatcc acgagcttat  480
ccacgagcat ccacgagctt atccgatttg agcattgatc tccatgagcc atttagtctc  540
accttcaaac tttagctcaa aatgcatgta tttattagtt taaactgaag gcgggaaacg  600
acaatctgat ccccatcaag ctagcttctg caggtcctgc tcgagcggcc gcagatcttg  660
agccaatcaa agaggagtga tgtagaccta aagcaataat ggagccatga cgtaagggct  720
tacgcccata cgaaataatt aaaggctgat gtgacctgtc ggtctctcag aacctttact  780
ttttatgttt ggcgtgtatt tttaaatttc cacggcaatg acgatgtgac ccaacgagat  840
cttgagccaa tcaaagagga gtgatgtaga cctaaagcaa taatggagcc atgacgtaag  900
ggcttacgcc catacgaaat aattaaaggc tgatgtgacc tgtcggtctc tcagaacctt  960
tactttttat atttggcgtg tatttttaaa tttccacggc aatgacgatg tgacctgtgc  1020
atccgctttg cctataaata agttttagtt tgtattgatc gacacggtcg agaagacacg  1080
gccataagct tggatcctcg agaattctca acacaacata tacaaaa               1127

SEQ ID NO: 12           moltype = DNA  length = 1355
FEATURE                 Location/Qualifiers
source                  1..1355
                        mol_type = other DNA
                        organism = synthetic construct
SEQUENCE: 12
atttaattag aatgcattca cattgtaatt cttttacatt attatttatt acctaattat  60
aaattatcaa caataaaatc tgacatagta tatgtttaga ttaaaatttg taaatgtaag  120
tttgaattaa aaaagtatat tataaacttg agtttggtat aatatttttt atcatcagac  180
tttggtataa tatgagttga tctaaaagta agttgaagga taccaaaggg taatctaaac  240
atgcatgaga aatgttgggg aatatcttta gtgtaaacaa aaagccttat aaattatcat  300
gtcatactat atatgacaaa tgttggtttt tgtaataatc attttaaata tgaacaacag  360
gattttcttt ttaccgtcaa aatatgaata aaagttaaac tcttaaatta ttgatcatag  420
gtttgcaatt ttttttata gagaggtttg caatttctga gttctcaata actgatgatt  480
aaatgcgcat cgtttgcatg catgaaaata aatttaagag gtaacatttg aagtctcacc  540
ttcatgtccg gggctgccag gaaagcttag atctccatga gcatccacga gcttatccac  600
gagcatccac gagcttatcc gatttgagca ttgatctcca tgagccattt agtctcacct  660
tcaaacactg atagtttaaa ctgaaggcgg gaaacgacaa tctgatcccc atcaagctag  720
cttctgcagg tcctgctcga gcggccgcag atcttgagcc aatcaaagag gagtgatgta  780
gacctaaagc aataatggag ccatgacgta agggcttacg cccatacgaa ataattaaag  840
gctgatgtga cctgtcggtc tctcagaacc tttacttttt atgtttggcg tgtattttta  900
aatttccacg gcaatgacga tgtgacccaa cgagatcttg agccaatcaa agaggagtga  960
tgtagaccta aagcaataat ggagccatga cgtaagggct tacgcccata cgaaataatt  1020
aaaggctgat gtgacctgtc ggtctctcag aacctttact ttttatattt ggcgtgtatt  1080
tttaaatttc cacggcaatg acgatgtgac ctgtgcatcc gctttgccta taaataagtt  1140
ttagtttgta ttgatcgaca cggtcgagaa gacacggcca taagcttgga tcctcgagaa  1200
ttctcaacac aacatataca aaacaaacga atctcaagca atcaagcatt ctacttctat  1260
tgcagcaatt taaatcattt cttttaaagc aaaagcaatt ttctgaaaat tttcaccatt  1320
tacgaacgat agccatggct tctatgatat cctct                             1355

SEQ ID NO: 13           moltype = DNA  length = 23
FEATURE                 Location/Qualifiers
source                  1..23
                        mol_type = other DNA
                        organism = synthetic construct
SEQUENCE: 13
```

```
gctcaaaatg catgtattta tta                                        23

SEQ ID NO: 14          moltype = DNA  length = 25
FEATURE                Location/Qualifiers
source                 1..25
                       mol_type = other DNA
                       organism = synthetic construct
SEQUENCE: 14
atttaattag aatgcattca cattg                                      25

SEQ ID NO: 15          moltype = DNA  length = 25
FEATURE                Location/Qualifiers
source                 1..25
                       mol_type = other DNA
                       organism = synthetic construct
SEQUENCE: 15
agaggatatc atagaagcca tggct                                      25

SEQ ID NO: 16          moltype = DNA  length = 1375
FEATURE                Location/Qualifiers
source                 1..1375
                       mol_type = other DNA
                       organism = synthetic construct
SEQUENCE: 16
atttaattag aatgcattca cattgtaatt cttttacatt attatttatt acctaattat  60
aaattatcaa caataaaatc tgacatagta tatgtttaga ttaaaatttg taaatgtaag  120
tttgaattaa aaaagtatat tataaacttg agtttggtat aatatttttt atcatcagac  180
tttggtataa tatgagttga tctaaaagta agttgaagga taccaaaggg taatctaaac  240
atgcatgaga aatgttgggg aatatcttta gtgtaaacaa aaagccttat aaattatcat  300
gtcatactat atatgacaaa tgttggtttt tgtaataatc attttaaata tgaacaacag  360
gattttcttt ttaccgtcaa aatatgaata aaagttaaac tcttaaatta ttgatcatag  420
gtttgcaatt ttttttata gagaggtttg caatttctga gttctcaata actgatgatt  480
aaatgcgcat cgtttgcatg catgaaaata aatttaagag gtaacatttg aagtctcacc  540
ttcatgtccg gggctgccag gaaagcttag atctccatga gcatccacga gcttatccac  600
gagcatccac gagcttatcc gatttgagca ttgatctcca tgagccattt agtctcacct  660
tcaaacttta gctcaaaatg catgtattta ttagtttaaa ctgaaggcgg gaaacgacaa  720
tctgatcccc atcaagctag cttctgcagg tcctgctcga gcggccgcag atcttgagcc  780
aatcaaagag gagtgatgta gacctaaagc aataatggag ccatgacgta agggcttacg  840
cccatacgaa ataattaaag gctgatgtga cctgtcggtc tctcagaacc tttacttttt  900
atgtttggcg tgtattttta aatttccacg gcaatgacga tgtgacccaa cgagatcttg  960
agccaatcaa agaggagtga tgtagaccta aagcaataat ggagccatga cgtaagggct  1020
tacgcccata cgaaataatt aaaggctgat gtgacctgtc ggtctctcag aacctttact  1080
ttttatattt ggcgtgtatt tttaaatttc cacggcaatg acgatgtgac ctgtgcatcc  1140
gctttgccta taaataagtt ttagtttgta ttgatcgaca cggtcgagaa gacacggcca  1200
taagcttgga tcctcgagaa ttctcaacac aacatataca aaacaaacga atctcaagca  1260
atcaagcatt ctacttctat tgcagcaatt taaatcattt cttttaaagc aaaagcaatt  1320
ttctgaaaat tttcaccatt tacgaacgat agccatggct tctatgatat cctct       1375

SEQ ID NO: 17          moltype = AA  length = 1307
FEATURE                Location/Qualifiers
source                 1..1307
                       mol_type = protein
                       organism = unidentified
SEQUENCE: 17
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 18          moltype = DNA  length = 40
FEATURE                Location/Qualifiers
```

```
source                  1..40
                        mol_type = other DNA
                        organism = synthetic construct
SEQUENCE: 18
tgagccattt agtctcacct tcaaacactg atagtttaaa                          40

SEQ ID NO: 19           moltype = DNA  length = 1126
FEATURE                 Location/Qualifiers
source                  1..1126
                        mol_type = other DNA
                        organism = synthetic construct
SEQUENCE: 19
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcacct                   1126

SEQ ID NO: 20           moltype = DNA  length = 40
FEATURE                 Location/Qualifiers
source                  1..40
                        mol_type = other DNA
                        organism = synthetic construct
SEQUENCE: 20
tccatgtaga tttcccggac tttagctcaa aatgcatgta                          40

SEQ ID NO: 21           moltype = DNA  length = 1817
FEATURE                 Location/Qualifiers
source                  1..1817
                        mol_type = other DNA
                        organism = synthetic construct
SEQUENCE: 21
tttagctcaa aatgcatgta tttattagcg ttctgtcttt tcgttaattt gttctcatca  60
taatattgtg acaaaaatat agctaggaaa gctttccatg catattttgt aagcaatgaa  120
gtatatagtg gatgcaatgt ctctatatat tcactagtcg agaaaattgc ggacagttct  180
gagattgatt ggcttcatgg ccctacggtg catctattac cattgtcttt gcatttgtca  240
tacaaaaagg tggaccatat tcatgttatg taaaaacaaa caaaatcacg cagtgcacat  300
cttctgcaga atgtgtaggt taaccttatt acacttgatt aagttaagtg tcatgccatt  360
agtttgagat tgaacttaaa atctttaatc aagatcttag atatggaaaa aattgtaatt  420
ccattaaaga taataagatt tttggataga aattaattat caattttaca ttaataacat  480
aataatttga agaaaaaaag taagggtcat aatcatacta accagagtaa tttgacacgt  540
gaaggggaca ctatgaaagc aaattacttt tggttcctaa aggttaggca agggaaagaa  600
agaatttgca cttaattagc actattttca aaattattat gtttcttttc cttatcttgc  660
ttaaaatttg cttattgtgt tattattatt attattgtta tgcatgatca attattcatc  720
aaagatcgat ctccaacctg ccaggaaatc cgctgatttg tttgcttcca atgtgagaga  780
tccaagatca gaattctgga aggtagtgct gactaccaag gtagcaaaat aatgatattg  840
gggaaggtga aaaatatgta gtactagtac ttctactaca aaatttcaaa aagggttttg  900
tgatttgtgc ataagaatct ttttgcattt gtctgtaagc ttgaaaatta cacgtggcac  960
aagtcacttg cagccaaaga acctttctgt gaccaattat gttccctgag ctgaatagtg  1020
gttcttattc taatctcatc aatatctaat tacctagtga atatactact agactattgc  1080
agtgttatta atatcttaat gatagactat tgcagcagac agaaattaca ggtattatta  1140
tatactaata tacaattctg cattttccac actttttcccc tgcccatgct tccatgccac  1200
tgaagtctga aaccacattg gcagattttg ctatctagaa attaaataac aatataagtt  1260
tgtatattta tatttcatat ttttttagta catttttatt ttgcacactc tataattcca  1320
tgattccttg attatcggag aatgatgtga tatgcaaacc acgagttaga accatcaaat  1380
caagcaaaga tatggatgga atgcctttaa tggaaagatt aattcaaagg ggcagaaact  1440
ggtaattttt tcttcaactg aatgctatgc agtatgcagc agatctttca tttacagaat  1500
atctgcaaaa ccttgtgttg gagatcttac ctattgaata atgatatagg taaaataaag  1560
tatttaattt caccataact tttaagatga tgttaaaatg atctatgcaa ttcatgttgg  1620
atcgaatatt aaagatgtca catctaatga tactatgata aaaataaagt ataatttctg  1680
atcttataag tcaaaataaa tcatgtaaat ataaattaat tctcttctta taaattaatt  1740
ttatataatt aagatagatc caatgtgaac tctaagacca tgcatatata aaaatcatta  1800
tcaagtgaat atgcaac                                                   1817

SEQ ID NO: 22           moltype = DNA  length = 5939
```

```
FEATURE                Location/Qualifiers
source                 1..5939
                       mol_type = other DNA
                       organism = synthetic construct
SEQUENCE: 22
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtt caaacactga tagtttaaac  1140
tgaaggcggg aaacgacaat ctgatcccca tcaagctagc ttctgcaggt cctgctcgag  1200
cggccgcaga tcttgagcca atcaaagagg agtgatgtag acctaaagca ataatggagc  1260
catgacgtaa gggcttacgc ccatacgaaa taattaaagg ctgatgtgac ctgtcggtct  1320
ctcagaacct ttacttttta tgtttggcgt gtatttttaa atttccacgg caatgacgat  1380
gtgacccaac gagatcttga gccaatcaaa gaggagtgat gtagacctaa agcaataatg  1440
gagccatgac gtaagggctt acgcccatac gaaataatta aaggctgatg tgacctgtcg  1500
gtctctcaga acctttactt tttatatttg gcgtgtattt ttaaatttcc acggcaatga  1560
cgatgtgacc tgtgcatccg ctttgcctat aaataagttt tagtttgtat tgatcgacac  1620
ggtcgagaag acacggccat aagcttggat cctcgagaat tctcaacaca acatatacaa  1680
aacaaacgaa tctcaagcaa tcaagcattc tacttctatt gcagcaattt aaatcatttc  1740
ttttaaagca aaagcaattt tctgaaaatt ttcaccattt acgaacgata gccatggctt  1800
ctatgatatc ctcttccgct gtgacaacag tcagccgtgc ctctaggggg caatccgccg  1860
caatggctcc attcggcggc ctcaaatcca tgactggatt cccagtgagg aaggtcaaca  1920
ctgacattac ttccattaca agcaatggtg gaagagtaaa gtgcatgcag gtgtggcctc  1980
caattggaaa gaagaagttt gagactcttt cctatttgcc accattgacg agagattccc  2040
gggccatggc caccttcgtc cgcaatgcct ggtatgtggc ggcgctgccc gaggaactgt  2100
ccgaaaagcc gctcggccgg acgattctcg acacaccgct cgcgctctac cgccagcccg  2160
acggtgtggt cgcggcgctg ctcgacatct gtccgcaccg cttcgcgccg ctgagcgacg  2220
gcatcctcgt caacggccat ctccaatgcc cctatcacgg gctggaattc gatggcggcg  2280
ggcagtgcgt ccataacccg cacggcaatg gcgcccgccc ggcttcgctc aacgtccgct  2340
ccttcccggt ggtggagcgc gacgcgctga tctggatctg tcccggcgat ccggcgctgg  2400
ccgatcctgg ggcgatcccc gacttcggct gccgcgtcga tcccgcctat cggaccgtcg  2460
gcggctatgg gcatgtcgac tgcaactaca agctgctggt cgacaacctg atggacctcg  2520
gccacgccca atatgtccat cgcgccaacg cccagaccga cgccttcgac cggctggagc  2580
gcgaggtgat cgtcggcgac ggtgagatac aggcgctgat gaagattccc ggcggcacgc  2640
cgagcgtgct gatggccaag ttcctgcgcg gcgccaatac ccccgtcgac gcttggaacg  2700
acatccgctg gaacaaggtg agcgcgatgc tcaacttcat cgcggtggcg ccggaaggca  2760
ccccgaagga gcagagcatc cactcgcgcg gtacccatat cctgaccccc gagacggagg  2820
cgagctgcca ttatttcttc ggctcctcgc gcaatttcgg catcgacgat ccggagatgg  2880
acggcgtgct gcgcagctgg caggctcagg cgctggtcaa ggaggacaag gtcgtcgtcg  2940
aggcgatcga gcgccgccgc gcctatgtcg aggcgaatgg catccgcccg gcgatgctgt  3000
cgtgcgacga agccgcagtc cgtgtcagcc gcgagatcga gaagcttgag cagctcgaag  3060
ccgcctgaac cggcttatgc tgcacgggcg gggcggggcg gtttcgatcg gctcgcctgt  3120
cccggcgata ttctagagct ttcgttcgta tcatcggttt cgacaacgtt cgtcaagttc  3180
aatgcatcag tttcattgcg cacacaccag aatcctactg agtttgagta ttatggcatt  3240
gggaaaactg tttttcttgt accatttgtt gtgcttgtaa tttactgtgt tttttattcg  3300
gttttcgcta tcgaactgtg aaatggaaat ggatggagaa gagttaatga atgatatggt  3360
ccttttgttc attctcaaat taatattatt tgtttttttct cttatttgtt gtgtgttgaa  3420
tttgaaatta taagagatat gcaaacattt tgttttgagt aaaaatgtgt caaatcgtgg  3480
cctctaatga ccgaagttaa tatgaggagt aaaacacttg tagttgtacc attatgctta  3540
ttcactaggc aacaaatata ttttcagacc tagaaaagct gcaaatgtta ctgaatacaa  3600
gtatgtcctc ttgtgtttta gacatttatg aactttcctt tatgtaattt tccagaatcc  3660
ttgtcagatt ctaatcattg ctttataatt atagttatac tcatggattt gtagttgagt  3720
atgaaaatat tttttaatgc attttatgac ttgccaattg attgacaaca tgcatcaatc  3780
gcggccgctc tagaactagt ggatccccc ctttaagggg gctgcaggaa ttcgatatca  3840
agctttggcg cgccaaatcg tgaagtttct catctaagcc cccatttgga cgtgaatgta  3900
gacacgtcga aataaagatt tccgaattag aataatttgt ttattgcttt cgcctataaa  3960
tacgacggat cgtaatttgt cgttttatca aaatgtactt tcattttata ataacgctgc  4020
ggacatctac atttttgaat tgaaaaaaaa ttggtaatta ctctttcttt ttctccatat  4080
tgaccatcat actcattgct gatccatgta gatttcccgg actttagctc aaaatgcatg  4140
tatttattag cgttctgtct tttcgttaat ttgttctcat cataatattg tgacaaaaat  4200
atagctagga aagctttcca tgcatatttt gtaagcaatg aagtatatag tggatgcaat  4260
gtctctatat attcactagt cgagaaaatt gcggacagtt ctgagattga ttggcttcat  4320
ggccctacgg tgcatctatt accattgtct ttgcatttgt catacaaaaa ggtggaccat  4380
attcatgtta tgtaaaaaca aacaaaatca cgcagtgcac atcttctgca gaatgtgtag  4440
```

```
gttaacctta ttacacttga ttaagttaag tgtcatgcca ttagtttgag attgaactta  4500
aaatctttaa tcaagatctt agatatggaa aaaattgtaa ttccattaaa gataataaga  4560
tttttggata gaaattaatt atcaatttta cattaataac ataataattt gaagaaaaaa  4620
agtaagggtc ataatcatac taaccagagt aatttgacac gtgaagggga cactatgaaa  4680
gcaaattact tttggttcct aaaggttagg caagggaaag aaagaatttg cacttaatta  4740
gcactatttt caaaattatt atgtttcttt tccttatctt gcttaaaatt tgcttattgt  4800
gttattatta ttattattgt tatgcatgat caattattca tcaaagatcg atctccaacc  4860
tgccaggaaa tccgctgatt tgtttgcttc caatgtgaga gatccaagat cagaattctg  4920
gaaggtagtg ctgactacca aggtagcaaa ataatgatat tggggaaggt gaaaaatatg  4980
tagtactagt acttctacta caaaatttca aaaagggttt tgtgatttgt gcataagaat  5040
ctttttgcat ttgtctgtaa gcttgaaaat tacacgtggc acaagtcact tgcagccaaa  5100
gaaccttttct gtgaccaatt atgttccctg agctgaatag tggttcttat tctaatctca  5160
tcaatatcta attacctagt gaatatacta ctagactatt gcagtgttat taatatctta  5220
atgatagact attgcagcag acagaaatta caggtattat tatatactaa tatacaattc  5280
tgcattttcc acacttttcc cctgcccatg cttccatgcc actgaagtct gaaaccacat  5340
tggcagattt tgctatctag aaattaaata acaatataag tttgtatatt tatatttcat  5400
atttttttag tacattttta ttttgcacac tctataattc catgattcct tgattatcgg  5460
agaatgatgt gatatgcaaa ccacgagtta gaaccatcaa atcaagcaaa gatatggatg  5520
gaatgccttt aatggaaaga ttaattcaaa ggggcagaaa ctggtaattt tttcttcaac  5580
tgaatgctat gcagtatgca gcagatcttt catttacaga atatctgcaa aaccttgtgt  5640
tggagatctt acctattgaa taatgatata ggtaaaataa agtatttaat ttcaccataa  5700
cttttaagat gatgttaaaa tgatctatgc aattcatgtt ggatcgaata ttaaagatgt  5760
cacatctaat gatactatga taaaaataaa gtataatttc tgatcttata agtcaaaata  5820
aatcatgtaa atataaatta attctcttct tataaattaa ttttatataa ttaagataga  5880
tccaatgtga actctaagac catgcatata taaaaatcat tatcaagtga atatgcaac   5939

SEQ ID NO: 23          moltype = DNA  length = 5966
FEATURE                Location/Qualifiers
source                 1..5966
                       mol_type = other DNA
                       organism = synthetic construct
SEQUENCE: 23
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaattttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtt tagctcaaaa tgcatgtatt  1140
tattattcaa acactgatag tttaaactga aggcgggaaa cgacaatctg atccccatca  1200
agctagcttc tgcaggtcct gctcgagcgg ccgcagatct tgagccaatc aaagaggagt  1260
gatgtagacc taaagcaata atggagccat gacgtaaggg cttacgccca tacgaaataa  1320
ttaaaggctg atgtgacctg tcggtctctc agaaccttta ctttttatgt ttggcgtgta  1380
tttttaaatt tccacggcaa tgacgatgtg acccaacgag atcttgagcc aatcaaagag  1440
gagtgatgta gacctaaagc aataatggag ccatgacgta agggcttacg cccatacgaa  1500
ataattaaag gctgatgtga cctgtcggtc tctcagaacc tttacttttt atatttggcg  1560
tgtattttta aatttccacg gcaatgacga tgtgacctgt gcatccgctt tgcctataaa  1620
taagttttag tttgtattga tcgacacggt cgagaagaca cggccataag cttggatcct  1680
cgagaattct caacacaaca tatacaaaac aaacgaatct caagcaatca agcattctac  1740
ttctattgca gcaatttaaa tcatttcttt taaagcaaaa gcaattttct gaaaattttc  1800
accatttacg aacgatagcc atggcttcta tgatatcctc ttccgctgtg acaacagtca  1860
gccgtgcctc tagggggcaa tccgccgcaa tggctccatt cggcggcctc aaatccatga  1920
ctggattccc agtgaggaag gtcaacactg acattacttc cattacaagc aatggtggaa  1980
gagtaaagtg catgcaggtg tggcctccaa ttggaaagaa gaagtttgag actctttcct  2040
atttgccacc attgacgaga gattcccggg ccatggccac cttcgtccgc aatgcctggt  2100
atgtggcggc gctgcccgag gaactgtccg aaaagccgct cggccggacg attctcgaca  2160
caccgctcgc gctctaccgc cagcccgacg gtgtggtcgc ggcgctgctc gacatctgtc  2220
cgcaccgctt cgcgccgctg agcgacggca tcctcgtcaa cggccatctc caatgcccct  2280
atcacgggct ggaattcgat ggcggcgggc agtgcgtcca taacccgcac ggcaatggcg  2340
cccgcccggc ttcgctcaac gtccgctcct tcccggtggt ggagcgcgac gcgctgatct  2400
ggatctgtcc cggcgatccg gcgctggccg atcctggggc gatccccgac ttcggctgcc  2460
gcgtcgatcc cgcctatcgg accgtcggcg gctatgggca tgtcgactgc aactacaagc  2520
tgctggtcga caacctgatg gacctcggcc acgcccaata tgtccatcgc gccaacgccc  2580
agaccgacgc cttcgaccgg ctggagcgcg aggtgatcgt cggcgacggt gagatacagg  2640
cgctgatgaa gattcccggc ggcacgccga gcgtgctgat ggccaagttc ctgcgcggcg  2700
ccaatacccc cgtcgacgct tggaacgaca tccgctggaa caaggtgagc gcgatgctca  2760
acttcatcgc ggtggcgccg gaaggcaccc cgaaggagca gagcatccac tcgcgcggta  2820
```

```
cccatatcct gacccccgag acggaggcga gctgccatta tttcttcggc tcctcgcgca  2880
atttcggcat cgacgatccg gagatggacg gcgtgctgcg cagctggcag gctcaggcgc  2940
tggtcaagga ggacaaggtc gtcgtcgagg cgatcgagcg ccgccgcgcc tatgtcgagg  3000
cgaatggcat ccgcccggcg atgctgtcgt gcgacgaagc cgcagtccgt gtcagccgcg  3060
agatcgagaa gcttgagcag ctcgaagccg cctgaaccgg cttatgctgc acgggcgggg  3120
cggggcggtt tcgatcggct cgcctgtccc ggcgatattc tagagctttc gttcgtatca  3180
tcggtttcga caacgttcgt caagttcaat gcatcagttt cattgcgcac acaccagaat  3240
cctactgagt ttgagtatta tggcattggg aaaactgttt ttcttgtacc atttgttgtg  3300
cttgtaattt actgtgtttt ttattcggtt ttcgctatcg aactgtgaaa tggaaatgga  3360
tggagaagag ttaatgaatg atatggtcct tttgttcatt ctcaaattaa tattatttgt  3420
tttttctctt atttgttgtg tgttgaattt gaaattataa gagatatgca aacattttgt  3480
tttgagtaaa aatgtgtcaa atcgtggcct ctaatgaccg aagttaatat gaggagtaaa  3540
acacttgtag ttgtaccatt atgcttattc actaggcaac aaatatattt tcagacctag  3600
aaaagctgca aatgttactg aatacaagta tgtcctcttg tgttttagac atttatgaac  3660
tttcctttat gtaattttcc agaatccttg tcagattcta atcattgctt tataattata  3720
gttatactca tggatttgta gttgagtatg aaaatatttt ttaatgcatt ttatgacttg  3780
ccaattgatt gacaacatgc atcaatcgcg gccgctctag aactagtgga tcccccccct  3840
taagggggct gcaggaattc gatatcaagc tttggcgcgc caaatcgtga agtttctcat  3900
ctaagccccc atttggacgt gaatgtagac acgtcgaaat aaagatttcc gaattagaat  3960
aatttgttta ttgctttcgc ctataaatac gacggatcgt aatttgtcgt tttatcaaaa  4020
tgtactttca ttttataata acgctgcgga catctacatt tttgaattga aaaaaaattg  4080
gtaattactc tttcttttc tccatattga ccatcatact cattgctgat ccatgtagat  4140
ttcccggact ttagctcaaa atgcatgtat ttattagcgt tctgtctttt cgttaatttg  4200
ttctcatcat aatattgtga caaaaatata gctaggaaag ctttccatgc atattttgta  4260
agcaatgaag tatatagtgg atgcaatgtc tctatatatt cactagtcga gaaaattgcg  4320
gacagttctg agattgattg gcttcatggc cctacggtgc atctattacc attgtctttg  4380
catttgtcat acaaaaaggt ggaccatatt catgttatgt aaaaacaaac aaaatcacgc  4440
agtgcacatc ttctgcagaa tgtgtaggtt aaccttatta cacttgatta agttaagtgt  4500
catgccatta gtttgagatt gaacttaaaa tctttaatca agatcttaga tatggaaaaa  4560
attgtaattc cattaaagat aataagattt ttggatagaa attaattatc aattttacat  4620
taataacata ataatttgaa gaaaaaaagt aagggtcata atcatactaa ccagagtaat  4680
ttgacacgtg aaggggacac tatgaaagca aattactttt ggttcctaaa ggttaggcaa  4740
gggaaagaaa gaatttgcac ttaattagca ctattttcaa aattattatg tttcttttcc  4800
ttatcttgct taaaatttgc ttattgtgtt attattatta ttattgttat gcatgatcaa  4860
ttattcatca aagatcgatc tccaacctgc caggaaatcc gctgatttgt ttgcttccaa  4920
tgtgagagat ccaagatcag aattctggaa ggtagtgctg actaccaagg tagcaaaata  4980
atgatattgg ggaaggtgaa aaatatgtag tactagtact tctactacaa aatttcaaaa  5040
agggttttgt gatttgtgca taagaatctt tttgcatttg tctgtaagct tgaaaattac  5100
acgtggcaca agtcacttgc agccaaagaa cctttctgtg accaattatg ttccctgagc  5160
tgaatagtgg ttcttattct aatctcatca atatctaatt acctagtgaa tatactacta  5220
gactattgca gtgttattaa tatcttaatg atagactatt gcagcagaca gaaattacag  5280
gtattattat atactaatat acaattctgc attttccaca cttttcccct gcccatgctt  5340
ccatgccact gaagtctgaa accacattgg cagattttgc tatctagaaa ttaaataaca  5400
atataagttt gtatatttat atttcatatt tttttagtac atttttattt tgcacactct  5460
ataattccat gattccttga ttatcggaga atgatgtgat atgcaaacca cgagttagaa  5520
ccatcaaatc aagcaaagat atggatggaa tgcctttaat ggaaagatta attcaaaggg  5580
gcagaaactg gtaatttttt cttcaactga atgctatgca gtatgcagca gatctttcat  5640
ttacagaata tctgcaaaac cttgtgttgg agatcttacc tattgaataa tgatataggt  5700
aaaataaagt atttaatttc accataactt ttaagatgat gttaaaatga tctatgcaat  5760
tcatgttgga tcgaatatta aagatgtcac atctaatgat actatgataa aaataaagta  5820
taatttctga tcttataagt caaaataaat catgtaaata taaattaatt ctcttcttat  5880
aaattaattt tatataatta agatagatcc aatgtgaact ctaagaccat gcatatataa  5940
aaatcattat caagtgaata tgcaac                                       5966
```

```
SEQ ID NO: 24          moltype = DNA  length = 1127
FEATURE                Location/Qualifiers
source                 1..1127
                       mol_type = other DNA
                       organism = synthetic construct
SEQUENCE: 24
aaaatttgta aatgtaagtt tgaattaaaa aagtatatta taaacttgag tttggtataa  60
tattttttat catcagactt tggtataata tgagttgatc taaaagtaag ttgaaggata  120
ccaaagggta atctaaacat gcatgagaaa tgttggggaa tatctttagt gtaaacaaaa  180
agccttataa attatcatgt catactatat atgacaaatg ttggtttttg taataatcat  240
tttaaatatg aacaacagga ttttcttttt accgtcaaaa tatgaataaa agttaaactc  300
ttaaattatt gatcataggt ttgcaatttt tttttataga gaggtttgca atttctgagt  360
tctcaataac tgatgattaa atgcgcatcg tttgcatgca tgaaaataaa tttaagaggt  420
aacatttgaa gtctcacctt catgtccggg gctgccagga aagcttagat ctccatgagc  480
atccacgagc ttatccacga gcatccacga gcttatccga tttgagcatt gatctccatg  540
agccatttag tttagctcaa aatgcatgta tttattattc aaacactgat agtttaaact  600
gaaggcggga aacgacaatc tgatccccat caagctagct tctgcaggtc ctgctcgagc  660
ggccgcagat cttgagccaa tcaaagagga gtgatgtaga cctaaagcaa taatggagcc  720
atgacgtaag ggcttacgcc catacgaaat aattaaaggc tgatgtgacc tgtcggtctc  780
tcagaacctt tactttttat gtttggcgtg tatttttaaa tttccacggc aatgacgatg  840
tgacccaacg agatcttgag ccaatcaaag aggagtgatg tagacctaaa gcaataatgg  900
agccatgacg taagggctta cgcccatacg aaataattaa aggctgatgt gacctgtcgg  960
tctctcagaa cctttacttt ttatatttgg cgtgtatttt taaatttcca cggcaatgac  1020
gatgtgacct gtgcatccgc tttgcctata aataagtttt agtttgtatt gatcgacacg  1080
gtcgagaaga cacggccata agcttggatc ctcgagaatt ctcaaca               1127
```

```
SEQ ID NO: 25          moltype = DNA  length = 5939
FEATURE                Location/Qualifiers
source                 1..5939
                       mol_type = other DNA
                       organism = synthetic construct
SEQUENCE: 25
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat ttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaatttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcaccttcaa acacttaaac  1140
tgaaggcggg aaacgacaat ctgatcccca tcaagctagc ttctgcaggt cctgctcgag  1200
cggccgcaga tcttgagcca atcaaagagg agtgatgtag acctaaagca ataatggagc  1260
catgacgtaa gggcttacgc ccatacgaaa taattaaagg ctgatgtgac ctgtcggtct  1320
ctcagaacct ttacttttta tgtttggcgt gtatttttaa atttccacgg caatgacgat  1380
gtgacccaac gagatcttga gccaatcaaa gaggagtgat gtagacctaa agcaataatg  1440
gagccatgac gtaagggctt acgcccatac gaaataatta aaggctgatg tgacctgtcg  1500
gtctctcaga acctttactt tttatatttg gcgtgtattt ttaaatttcc acggcaatga  1560
cgatgtgacc tgtgcatccg ctttgcctat aaataagttt tagtttgtat tgatcgacac  1620
ggtcgagaag acacggccat aagcttggat cctcgagaat tctcaacaca acatatacaa  1680
aacaaacgaa tctcaagcaa tcaagcattc tacttctatt gcagcaattt aaatcatttc  1740
ttttaaagca aaagcaattt tctgaaaatt ttcaccattt acgaacgata gccatggctt  1800
ctatgatatc ctcttccgct gtgacaacag tcagccgtgc ctctaggggg caatccgccg  1860
caatggctcc attcggcggc ctcaaatcca tgactggatt cccagtgagg aaggtcaaca  1920
ctgacattac ttccattaca agcaatggtg gaagagtaaa gtgcatgcag gtgtggcctc  1980
caattggaaa gaagaagttt gagactcttt cctatttgcc accattgacg agagattccc  2040
gggccatggc caccttcgtc cgcaatgcct ggtatgtggc ggcgctgccc gaggaactgt  2100
ccgaaaagcc gctcggccgg acgattctcg acacaccgct cgcgctctac cgccagcccg  2160
acggtgtggt cgcggcgctg ctcgacatct gtccgcaccg cttcgcgccg ctgagcgacg  2220
gcatcctcgt caacggccat ctccaatgcc cctatcacgg gctggaattc gatggcggcg  2280
ggcagtgcgt ccataacccg cacggcaatg gcgcccgccc ggcttcgctc aacgtccgct  2340
ccttcccggt ggtggagcgc gacgcgctga tctggatctg tcccggcgat ccggcgctgg  2400
ccgatcctgg ggcgatcccc gacttcggct gccgcgtcga tcccgcctat cggaccgtcg  2460
gcggctatgg gcatgtcgac tgcaactaca agctgctggt cgacaacctg atggacctcg  2520
gccacgccca atatgtccat cgcgccaacg cccagaccga cgccttcgac cggctggagc  2580
gcgaggtgat cgtcggcgac ggtgagatac aggcgctgat gaagattccc ggcggcacgc  2640
cgagcgtgct gatggccaag ttcctgcgcg gcgccaatac cccgtcgac gcttggaacg  2700
acatccgctg gaacaaggtg agcgcgatgc tcaacttcat cgcggtggcg ccggaaggca  2760
ccccgaagga gcagagcatc cactcgcgcg gtacccatat cctgaccccc gagacggagg  2820
cgagctgcca ttatttcttc ggctcctcgc gcaatttcgg catcgacgat ccggagatgg  2880
acggcgtgct gcgcagctgg caggctcagg cgctggtcaa ggaggacaag gtcgtcgtcg  2940
aggcgatcga gcgccgccgc gcctatgtcg aggcgaatgg catccgcccg gcgatgctgt  3000
cgtgcgacga agccgcagtc cgtgtcagcc gcgagatcga gaagcttgag cagctcgaag  3060
ccgcctgaac cggcttatgc tgcacgggcg gggcggggcg gtttcgatcg gctcgcctgt  3120
cccggcgata ttctagagct ttcgttcgta tcatcggttt cgacaacgtt cgtcaagttc  3180
aatgcatcag tttcattgcg cacacaccag aatcctactg agtttgagta ttatggcatt  3240
gggaaaactg tttttcttgt accatttgtt gtgcttgtaa tttactgtgt tttttattcg  3300
gttttcgcta tcgaactgtg aaatggaaat ggatggagaa gagttaatga atgatatggt  3360
ccttttgttc attctcaaat taatattatt tgttttttct cttatttgtt gtgtgttgaa  3420
tttgaaatta taagagatat gcaaacattt tgttttgagt aaaaatgtgt caaatcgtgg  3480
cctctaatga ccgaagttaa tatgaggagt aaaacacttg tagttgtacc attatgctta  3540
ttcactaggc aacaaatata ttttcagacc tagaaaagct gcaaatgtta ctgaatacaa  3600
gtatgtcctc ttgtgtttta gacatttatg aactttcctt tatgtaattt tccagaatcc  3660
ttgtcagatt ctaatcattg ctttataatt atagttatac tcatggattt gtagttgagt  3720
atgaaaatat tttttaatgc attttatgac ttgccaattg attgacaaca tgcatcaatc  3780
gcggccgctc tagaactagt ggatcccccc ctttaagggg gctgcaggaa ttcgatatca  3840
agctttggcg cgccaaatcg tgaagtttct catctaagcc cccatttgga cgtgaatgta  3900
gacacgtcga aataaagatt tccgaattag aataatttgt ttattgcttt cgcctataaa  3960
tacgacggat cgtaatttgt cgttttatca aaatgtactt tcattttata ataacgctgc  4020
ggacatctac atttttgaat tgaaaaaaaa ttggtaatta ctctttcttt ttctccatat  4080
tgaccatcat actcattgct gatccatgta gatttcccgg actttagctc aaaatgcatg  4140
tatttattag cgttctgtct tttcgttaat ttgttctcat cataatattg tgacaaaaat  4200
atagctagga aagctttcca tgcatatttt gtaagcaatg aagtatatag tggatgcaat  4260
gtctctatat attcactagt cgagaaaatt gcggacagtt ctgagattga ttggcttcat  4320
```

```
ggccctacgg tgcatctatt accattgtct ttgcatttgt catacaaaaa ggtggaccat  4380
attcatgtta tgtaaaaaca aacaaaatca cgcagtgcac atcttctgca gaatgtgtag  4440
gttaacctta ttacacttga ttaagttaag tgtcatgcca ttagtttgag attgaactta  4500
aaatctttaa tcaagatctt agatatggaa aaaattgtaa ttccattaaa gataataaga  4560
tttttggata gaaattaatt atcaatttta cattaataac ataataattt gaagaaaaaa  4620
agtaagggtc ataatcatac taaccagagt aatttgacac gtgaagggga cactatgaaa  4680
gcaaattact tttggttcct aaaggttagg caagggaaag aaagaatttg cacttaatta  4740
gcactatttt caaaattatt atgtttcttt tccttatctt gcttaaaatt tgcttattgt  4800
gttattatta ttattattgt tatgcatgat caattattca tcaaagatcg atctccaacc  4860
tgccaggaaa tccgctgatt tgtttgcttc caatgtgaga gatccaagat cagaattctg  4920
gaaggtagtg ctgactacca aggtagcaaa ataatgatat tggggaaggt gaaaaaatatg  4980
tagtactagt acttctacta caaaatttca aaaagggttt tgtgatttgt gcataagaat  5040
ctttttgcat ttgtctgtaa gcttgaaaat tacacgtggc acaagtcact tgcagccaaa  5100
gaacctttct gtgaccaatt atgttccctg agctgaatag tggttcttat tctaatctca  5160
tcaatatcta attacctagt gaatatacta ctagactatt gcagtgttat taatatctta  5220
atgatagact attgcagcag acagaaatta caggtattat tatatactaa tatacaattc  5280
tgcattttcc acacttttcc cctgcccatg cttccatgcc actgaagtct gaaaccacat  5340
tggcagattt tgctatctag aaattaaata acaatataag tttgtatatt tatatttcat  5400
attttttag tacattttta ttttgcacac tctataattc catgattcct tgattatcgg  5460
agaatgatgt gatatgcaaa ccacgagtta gaaccatcaa atcaagcaaa gatatggatg  5520
gaatgccttt aatggaaaga ttaattcaaa ggggcagaaa ctggtaattt tttcttcaac  5580
tgaatgctat gcagtatgca gcagatcttt catttacaga atatctgcaa aaccttgtgt  5640
tggagatctt acctattgaa taatgatata ggtaaaataa agtatttaat ttcaccataa  5700
cttttaagat gatgttaaaa tgatctatgc aattcatgtt ggatcgaata ttaaagatgt  5760
cacatctaat gatactatga taaaaataaa gtataatttc tgatcttata agtcaaaata  5820
aatcatgtaa atataaatta attctcttct tataaattaa ttttatataa ttaagataga  5880
tccaatgtga actctaagac catgcatata taaaaatcat tatcaagtga atatgcaac   5939

SEQ ID NO: 26           moltype = DNA  length = 5966
FEATURE                 Location/Qualifiers
source                  1..5966
                        mol_type = other DNA
                        organism = synthetic construct
SEQUENCE: 26
gtacaaataa aactttatct gtacatttcg ttagttaaat tatattttgt ccatcaaatt  60
gttcctttaa attaaaatct aaaaactaac tttaccgtaa agaaatatgc attcatgtat  120
accaaataaa attttgacaa gagtttaagt tttatattat gattcttaag gaaatcatta  180
tcattataat tttataaaaat aaataaattg ataattatat gctatatcaa tttatgattt  240
gatgagtatg tatgttttaa atgcgagatt ctgccgccgt tcgatatagt tagcagtaga  300
gccctgttct caccctcaca cctgctcagt gtgaacttta aaagggactt tgttgacaaa  360
tgttaggatc gtcgtcttct tttgcaataa aaaatttttca tctgtttaaa acgtttttat  420
agtaaaatta taaatagaaa atttagttgt aaaatttgaa atataaattt aattagaatg  480
cattcacatt gtaattcttt tacattatta tttattacct aattataaat tatcaacaat  540
aaaatctgac atagtatatg tttagattaa aatttgtaaa tgtaagtttg aattaaaaaa  600
gtatattata aacttgagtt tggtataata ttttttatca tcagactttg gtataatatg  660
agttgatcta aaagtaagtt gaaggatacc aaagggtaat ctaaacatgc atgagaaatg  720
ttggggaata tctttagtgt aaacaaaaag ccttataaat tatcatgtca tactatatat  780
gacaaatgtt ggtttttgta ataatcattt taaatatgaa caacaggatt ttctttttac  840
cgtcaaaata tgaataaaag ttaaactctt aaattattga tcataggttt gcaatttttt  900
tttatagaga ggtttgcaat ttctgagttc tcaataactg atgattaaat gcgcatcgtt  960
tgcatgcatg aaaataaatt taagaggtaa catttgaagt ctcaccttca tgtccggggc  1020
tgccaggaaa gcttagatct ccatgagcat ccacgagctt atccacgagc atccacgagc  1080
ttatccgatt tgagcattga tctccatgag ccatttagtc tcaccttcaa acactttagc  1140
tcaaaatgca tgtatttatt attaaactga aggcgggaaa cgacaatctg atccccatca  1200
agctagcttc tgcaggtcct gctcgagcgg ccgcagatct tgagccaatc aaagaggagt  1260
gatgtagacc taaagcaata atggagccat gacgtaaggg cttacgccca tacgaaataa  1320
ttaaaggctg atgtgacctg tcggtctctc agaaccttta ctttttatgt ttggcgtgta  1380
tttttaaatt tccacggcaa tgacgatgtg acccaacgag atcttgagcc aatcaaagag  1440
gagtgatgta gacctaaagc aataatggag ccatgacgta agggcttacg cccatacgaa  1500
ataattaaag gctgatgtga cctgtcggtc tctcagaacc tttacttttt atatttggcg  1560
tgtattttta aatttccacg gcaatgacga tgtgacctgt gcatccgctt tgcctataaa  1620
taagttttag tttgtattga tcgacacggt cgagaagaca cggccataag cttggatcct  1680
cgagaattct caacacaaca tatacaaaac aaacgaatct caagcaatca agcattctac  1740
ttctattgca gcaatttaaa tcatttcttt taaagcaaaa gcaattttct gaaaattttc  1800
accatttacg aacgatagcc atggcttcta tgatatcctc ttccgctgtg acaacagtca  1860
gccgtgcctc tagggggcaa tccgccgcaa tggctccatt cggcggcctc aaatccatga  1920
ctggattccc agtgaggaag gtcaacactg acattacttc cattacaagc aatggtggaa  1980
gagtaaagtg catgcaggtg tggcctccaa ttggaaagaa gaagtttgag actctttcct  2040
atttgccacc attgacgaga gattcccggg ccatggccac cttcgtccgc aatgcctggt  2100
atgtggcggc gctgcccgag gaactgtccg aaaagccgct cggccggacg attctcgaca  2160
caccgctcgc gctctaccgc cagcccgacg gtgtggtcgc ggcgctgctc gacatctgtc  2220
cgcaccgctt cgcgccgctg agcgacggca tcctcgtcaa cggccatctc caatgcccct  2280
atcacgggct ggaattcgat ggcggcgggc agtgcgtcca taacccgcac ggcaatggcg  2340
cccgcccggc ttcgctcaac gtccgctcct tcccggtggt ggagcgcgac gcgctgatct  2400
ggatctgtcc cggcgatccg gcgctggccg atcctggggc gatccccgac ttcggctgcc  2460
gcgtcgatcc cgcctatcgg accgtcggcg gctatgggca tgtcgactgc aactacaagc  2520
tgctggtcga caacctgatg gacctcggcc acgcccaata tgtccatcgc gccaacgccc  2580
agaccgacgc cttcgaccgg ctggagcgcg aggtgatcgt cggcgacggt gagatacagg  2640
cgctgatgaa gattcccggc ggcacgccga gcgtgctgat ggccaagttc ctgcgcggcg  2700
```

```
ccaatacccc cgtcgacgct tggaacgaca tccgctggaa caaggtgagc gcgatgctca  2760
acttcatcgc ggtggcgccg gaaggcaccc cgaaggagca gagcatccac tcgcgcggta  2820
cccatatcct gacccccgag acggaggcga gctgccatta tttcttcggc tcctcgcgca  2880
atttcggcat cgacgatccg gagatggacg gcgtgctgcg cagctggcag gctcaggcgc  2940
tggtcaagga ggacaaggtc gtcgtcgagg cgatcgagcg ccgccgcgcc tatgtcgagg  3000
cgaatggcat ccgcccggcg atgctgtcgt gcgacgaagc cgcagtccgt gtcagccgcg  3060
agatcgagaa gcttgagcag ctcgaagccg cctgaaccgg cttatgctgc acgggcgggg  3120
cggggcggtt tcgatcggct cgcctgtccc ggcgatattc tagagctttc gttcgtatca  3180
tcggtttcga caacgttcgt caagttcaat gcatcagttt cattgcgcac acaccagaat  3240
cctactgagt ttgagtatta tggcattggg aaaactgttt ttcttgtacc atttgttgtg  3300
cttgtaattt actgtgtttt ttattcggtt ttcgctatcg aactgtgaaa tggaaatgga  3360
tggagaagag ttaatgaatg atatggtcct tttgttcatt ctcaaattaa tattatttgt  3420
tttttctctt atttgttgtg tgttgaattt gaaattataa gagatatgca aacattttgt  3480
tttgagtaaa aatgtgtcaa atcgtggcct ctaatgaccg aagttaatat gaggagtaaa  3540
acacttgtag ttgtaccatt atgcttattc actaggcaac aaatatattt tcagacctag  3600
aaaagctgca aatgttactg aatacaagta tgtcctcttg tgttttagac atttatgaac  3660
tttcctttat gtaattttcc agaatccttg tcagattcta atcattgctt tataattata  3720
gttatactca tggatttgta gttgagtatg aaaatatttt ttaatgcatt ttatgacttg  3780
ccaattgatt gacaacatgc atcaatcgcg gccgctctag aactagtgga tccccccctt  3840
taagggggct gcaggaattc gatatcaagc tttggcgcgc caaatcgtga agtttctcat  3900
ctaagccccc atttggacgt gaatgtagac acgtcgaaat aaagatttcc gaattagaat  3960
aatttgttta ttgctttcgc ctataaatac gacggatcgt aatttgtcgt tttatcaaaa  4020
tgtactttca ttttataata acgctgcgga catctacatt tttgaattga aaaaaaattg  4080
gtaattactc tttcttttc tccatattga ccatcatact cattgctgat ccatgtagat  4140
ttcccggact ttagctcaaa atgcatgtat ttattagcgt tctgtctttt cgttaatttg  4200
ttctcatcat aatattgtga caaaaatata gctaggaaag ctttccatgc atattttgta  4260
agcaatgaag tatatagtgg atgcaatgtc tctatatatt cactagtcga gaaaattgcg  4320
gacagttctg agattgattg gcttcatggc cctacggtgc atctattacc attgtctttg  4380
catttgtcat acaaaaaggt ggaccatatt catgttatgt aaaaacaaac aaaatcacgc  4440
agtgcacatc ttctgcagaa tgtgtaggtt aaccttatta cacttgatta agttaagtgt  4500
catgccatta gtttgagatt gaacttaaaa tctttaatca agatcttaga tatggaaaaa  4560
attgtaattc cattaaagat aataagattt ttggatagaa attaattatc aattttacat  4620
taataacata ataatttgaa gaaaaaaagt aagggtcata atcatactaa ccagagtaat  4680
ttgacacgtg aaggggacac tatgaaagca aattactttt ggttcctaaa ggttaggcaa  4740
gggaaagaaa gaatttgcac ttaattagca ctattttcaa aattattatg tttcttttcc  4800
ttatcttgct taaaatttgc ttattgtgtt attattatta ttattgttat gcatgatcaa  4860
ttattcatca aagatcgatc tccaacctgc caggaaatcc gctgatttgt ttgcttccaa  4920
tgtgagagat ccaagatcag aattctggaa ggtagtgctg actaccaagg tagcaaaata  4980
atgatattgg ggaaggtgaa aaatatgtag tactagtact tctactacaa aatttcaaaa  5040
agggttttgt gatttgtgca taagaatctt tttgcatttg tctgtaagct tgaaaattac  5100
acgtggcaca agtcacttgc agccaaagaa cctttctgtg accaattatg ttccctgagc  5160
tgaatagtgg ttcttattct aatctcatca atatctaatt acctagtgaa tatactacta  5220
gactattgca gtgttattaa tatcttaatg atagactatt gcagcagaca gaaattacag  5280
gtattattat atactaatat acaattctgc attttccaca cttttcccct gcccatgctt  5340
ccatgccact gaagtctgaa accacattgg cagattttgc tatctagaaa ttaaataaca  5400
atataagttt gtatatttat atttcatatt tttttagtac atttttattt tgcacactct  5460
ataattccat gattccttga ttatcggaga atgatgtgat atgcaaacca cgagttagaa  5520
ccatcaaatc aagcaaagat atggatggaa tgcctttaat ggaaagatta attcaaaggg  5580
gcagaaactg gtaatttttt cttcaactga atgctatgca gtatgcagca gatctttcat  5640
ttacagaata tctgcaaaac cttgtgttgg agatcttacc tattgaataa tgatataggt  5700
aaaataaagt atttaatttc accataactt ttaagatgat gttaaaatga tctatgcaat  5760
tcatgttgga tcgaatatta aagatgtcac atctaatgat actatgataa aaataaagta  5820
taatttctga tcttataagt caaaataaat catgtaaata taaattaatt ctcttcttat  5880
aaattaattt tatataatta agatagatcc aatgtgaact ctaagaccat gcatatataa  5940
aaatcattat caagtgaata tgcaac                                        5966
```

```
SEQ ID NO: 27          moltype = DNA  length = 1127
FEATURE                Location/Qualifiers
source                 1..1127
                       mol_type = other DNA
                       organism = synthetic construct
SEQUENCE: 27
aaaatttgta aatgtaagtt tgaattaaaa aagtatatta taaacttgag tttggtataa  60
tattttttat catcagactt tggtataata tgagttgatc taaaagtaag ttgaaggata  120
ccaaagggta atctaaacat gcatgagaaa tgttggggaa tatctttagt gtaaacaaaa  180
agccttataa attatcatgt catactatat atgacaaatg ttggtttttg taataatcat  240
tttaaatatg aacaacagga ttttcttttt accgtcaaaa tatgaataaa agttaaactc  300
ttaaattatt gatcataggt ttgcaatttt tttttataga gaggtttgca atttctgagt  360
tctcaataac tgatgattaa atgcgcatcg tttgcatgca tgaaaataaa tttaagaggt  420
aacatttgaa gtctcacctt catgtccggg gctgccagga aagcttagat ctccatgagc  480
atccacgagc ttatccacga gcatccacga gcttatccga tttgagcatt gatctccatg  540
agccatttag tctcaccttc aaacacttta gctcaaaatg catgtattta ttattaaact  600
gaaggcggga aacgacaatc tgatccccat caagctagct tctgcaggtc ctgctcgagc  660
ggccgcagat cttgagccaa tcaaagagga gtgatgtaga cctaaagcaa taatggagcc  720
atgacgtaag ggcttacgcc catacgaaat aattaaaggc tgatgtgacc tgtcggtctc  780
tcagaacctt tactttttat gtttggcgtg tatttttaaa tttccacggc aatgacgatg  840
tgacccaacg agatcttgag ccaatcaaag aggagtgatg tagacctaaa gcaataatgg  900
agccatgacg taagggctta cgcccatacg aaataattaa aggctgatgt gacctgtcgg  960
tctctcagaa cctttacttt ttatatttgg cgtgtatttt taaatttcca cggcaatgac  1020
```

-continued

```
gatgtgacct gtgcatccgc tttgcctata aataagtttt agtttgtatt gatcgacacg  1080
gtcgagaaga cacggccata agcttggatc ctcgagaatt ctcaaca                1127
```

MODIFIED EXCISABLE MON87708 SOYBEAN TRANSGENIC HERBICIDE RESISTANCE LOCUS

CROSS-REFERENCE TO RELATED APPLICATIONS

This is a continuation application of International Application No. PCT/US2021/043,897, filed on Jul. 30, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, each of which are incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 18, 2022, is named "P13648US00_SequenceListing.xml" and is 76,771 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An examples of a selected transgenic soybean event which confers herbicide tolerance is the MON87708 transgenic soybean event disclosed in U.S. Pat. No. 9,447,428. MON87708 transgenic soybean plants express a dicamba mono-oxygenase (DMO) protein which confers tolerance to the herbicide dicamba.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic soybean plant cells comprising an INHT30 transgenic locus comprising an originator guide RNA recognition site (OgRRS) in a first DNA junction polynucleotide of a MON87708 transgenic locus and a cognate guide RNA recognition site (CgRRS) in a second DNA junction polynucleotide of the MON87708 transgenic locus are provided. Transgenic soybean plant cells comprising an INHT30 transgenic locus comprising an insertion and/or substitution in a DNA junction polynucleotide of a MON87708 transgenic locus of DNA comprising a cognate guide RNA recognition site (CgRRS) are provided. In certain embodiments, the MON87708 transgenic locus is set forth in SEQ ID NO:1, is present in seed deposited at the ATCC under accession No. PTA-9670, is present in progeny thereof, is present in allelic variants thereof, or is present in other variants thereof. INHT30 transgenic soybean plant cells, transgenic soybean plant seeds, and transgenic soybean plants all comprising a transgenic locus set forth in SEQ ID NO: 2, 3, 22, 23, 25, 26, or an allelic variant thereof are provided. Transgenic soybean plant parts including seeds and transgenic soybean plants comprising the soybean plant cells are also provided.

Methods for obtaining a bulked population of inbred seed comprising selfing the aforementioned transgenic soybean plants and harvesting seed comprising the INHT30 transgenic locus from the selfed soybean plant are also provided.

Methods of obtaining hybrid soybean seed comprising crossing the aforementioned transgenic soybean plants to a second soybean plant which is genetically distinct from the first soybean plant and harvesting seed comprising the INHT30 transgenic locus from the cross are provided. Methods for obtaining a bulked population of seed comprising selfing a transgenic soybean plant of comprising SEQ ID NO: 2, 3, 22, 23, 25, 26, or an allelic variant thereof and harvesting transgenic seed comprising the transgenic locus set forth in SEQ ID NO: 3 or an allelic variant thereof are provided.

A DNA molecule comprising SEQ ID NO: 2, 3, 8, 9, 10, 11, 16, 22, 23, 24, 25, 26, 27, or an allelic variant thereof is provided. Processed transgenic soybean plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a soybean plant cell comprising an INHT30 transgenic locus, comprising the step of detecting a DNA molecule comprising SEQ ID NO:2, 3, 8, 9, 10, 11, 16, 22, 23, 24, 25, 26, 27, or an allelic variant thereof, are provided.

Methods of excising the INHT30 transgenic locus from the genome of the aforementioned soybean plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INHT30 transgenic locus flanked by the OgRRS and the CgRRS has been excised.

BRIEF DESCRIPTION OF THE DRAWINGS/FIGURES

FIG. 1 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") with genome editing molecules.

Figure 2A:
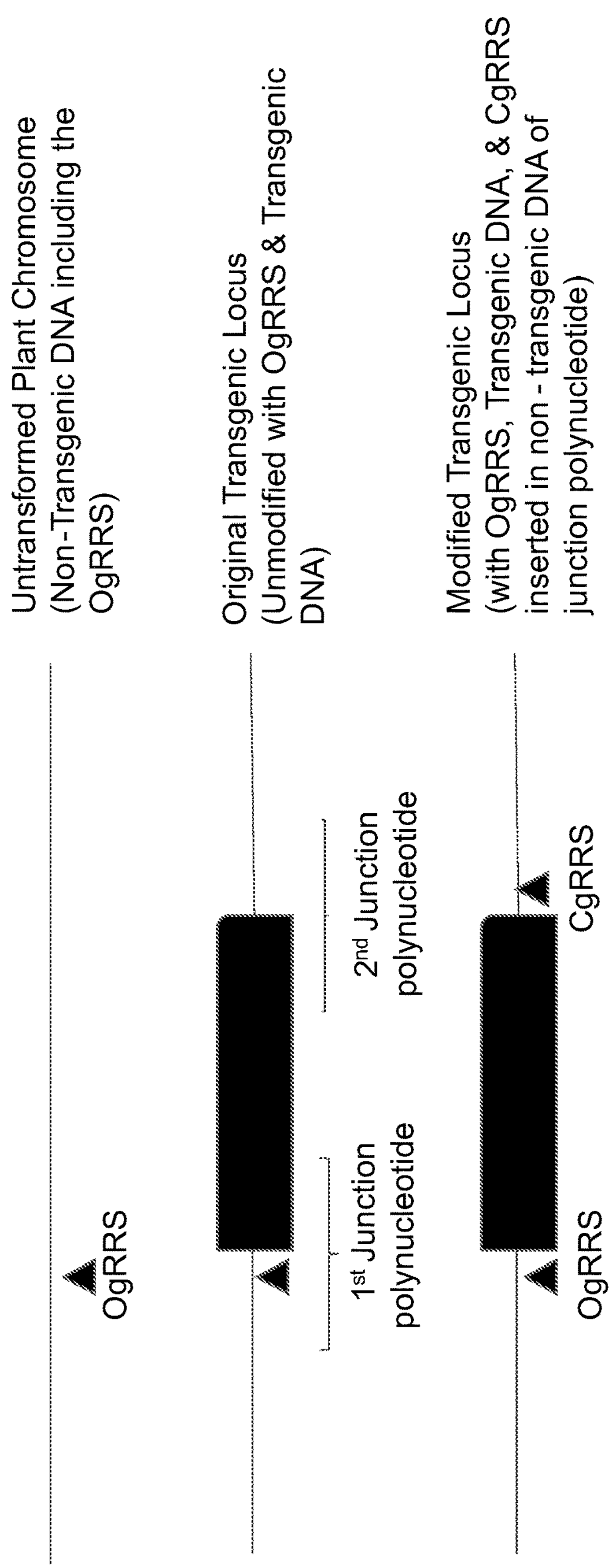
Figure 2B:
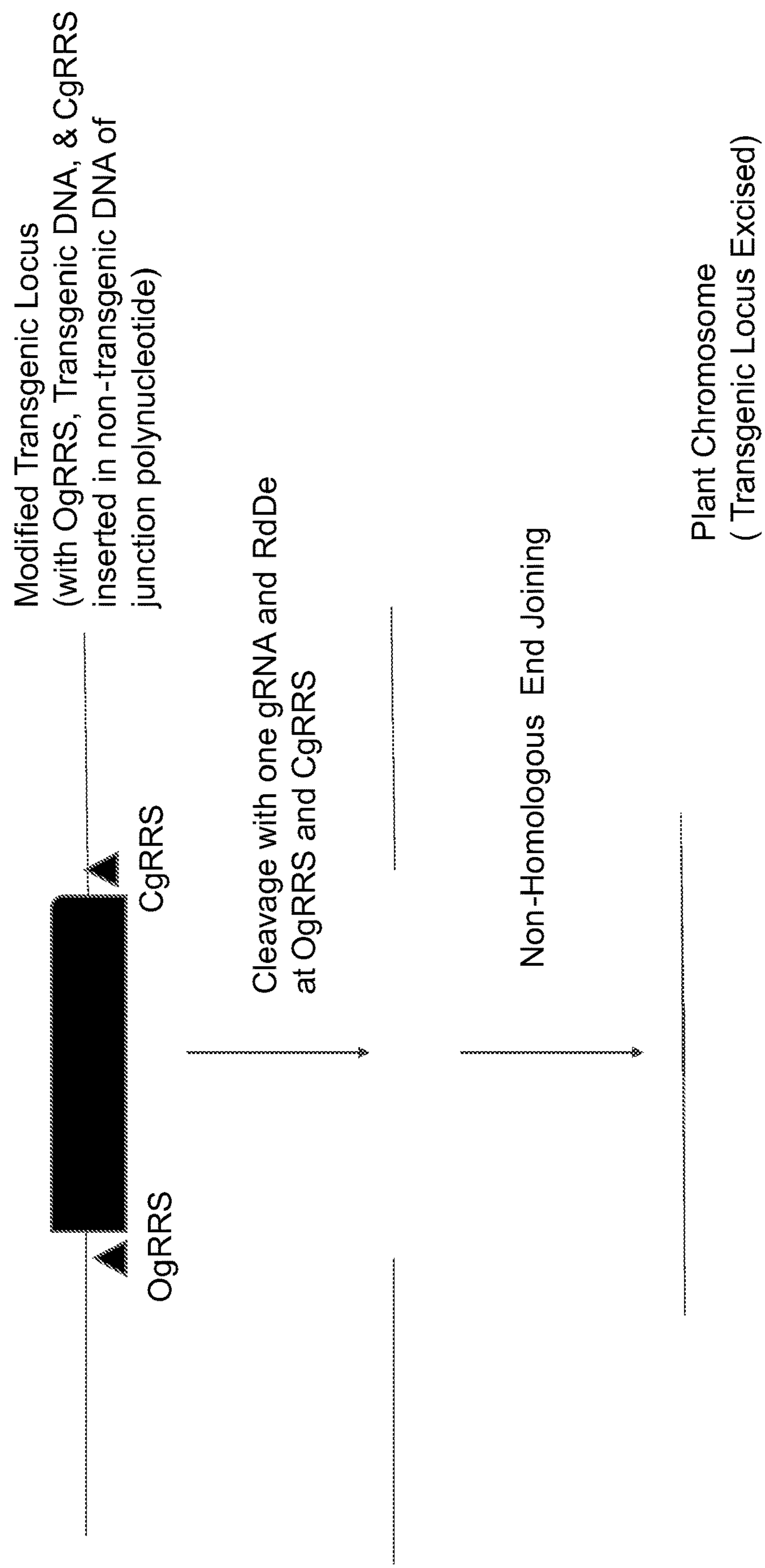
Figure 2C:
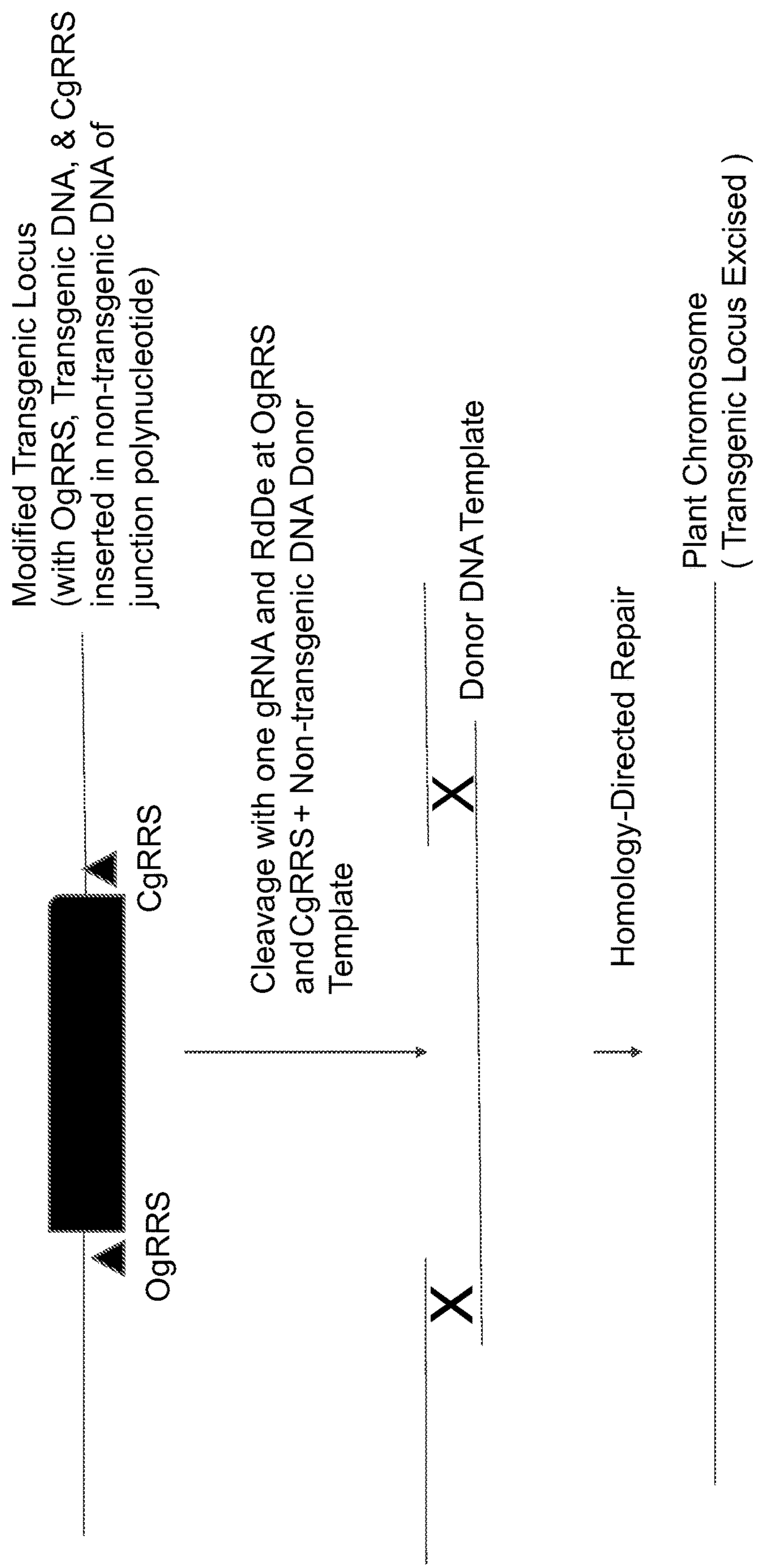

FIG. 2A, B, C. FIG. 2A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 2B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 2C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 2C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 17.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "MON87708" is used to refer to any of a transgenic soybean locus, transgenic soybean plants and parts thereof including seed set forth in U.S. Pat. No. 9,447,428, which is incorporated herein by reference in its entirety. Representative MON87708 transgenic soybean seed have been deposited with American Type Culture Collection (ATCC, Manassas, Va. 20110-2209 USA) under Accession No. PTA-9670. MON87708 transgenic loci include loci having the sequence of SEQ ID NO:1, the sequence of the MON87708 locus in the deposited seed of Accession No. PTA-9670 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INHT30" is used to refer either individually collectively to items that include any or all of the MON87708 transgenic soybean loci which have been modified as disclosed herein, modified MON87708 transgenic soybean plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in non-transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
|---|---|
| 1 | MON87708 Complete Transgenic Locus comprising from 5' to 3':5' flanking plant genomic DNA; 5' junction polynucleotide; Peanut Chlorotic Streak Virus (PC1SV) promoter with a duplicated enhancer region (P-PCISV.FLt-enh); Tobacco Etch Virus (L-TEV) 5' UTR; Pisum sativum (TS-RbcS-3C) N-terminal chloroplast transit peptide and portion of mature protein coding sequence; a dicamba mono-oxygenase (DMO)coding sequence; a Pisum sativum (T-Ps.RbcS2-E9) 3' UTR; 3' junction polynucleotide, and 3' flanking plant genomic DNA. The MON87708 5' flank region comprises nucleotides 1-1126 of SEQ ID NO: 1. The MON87708 transgenic insert extends from nucleotides 1127-4129 of SEQ ID NO: 1. The MON87708 3' flanking DNA comprises 4130-5946 of SEQ ID NO: 1. |
| 2 | INHT30-1 (with gRNA-2 Cut resulting in a deletion of nucleotides in a MON87708 5' junction polynucleotide sequence) |
| 3 | INHT30-2 (Insertion of 27 bp CgRRS with gRNA-2 Cut and with SEQ ID NO: 11 donor DNA template) |
| 4 | gRNA-1 coding |
| 5 | gRNA-2 coding |
| 6 | gRNA-3 coding |
| 7 | OgRRS |
| 8 | CgRRS+ Flanking DNA (G1 Insert) |
| 9 | CgRRS+ Flanking DNA (G2 Insert) |
| 10 | CgRRS+ Flanking DNA (G3 Insert) |
| 11 | MON87708 CgRRS DNA donor template sequence containing the SEQ ID NO: 9 CgRRS |
| 12 | MON87708 5' target insertion site |
| 13 | MON87708-gRNA spacer coding sequence that targets CgRRS of SEQ ID NO: 8, 9, 10 and OgRRS of SEQ ID NO: 7 |
| 14 | MON87708 5' primer |
| 15 | MON87708 3' primer |
| 16 | MON87708 CgRRS and flank PCR amplicon from SEQ ID NO: 3 template using SEQ ID NO: 14 and 15 primers |
| 17 | (Cas 12a Nuclease ) (>sp\|U2UMQ6\|CS12A_ACISB CRISPR-associated endonuclease Casl2a OS=Acidaminococcus sp. (strain BV3L6) OX = 1111120 GN = casl2a PE = 1 SV = 1) |
| 18 | MON87708 transgenic locus 5' Junction Polynucleotide |
| 19 | MON87708 transgenic locus 5' plant genomic flanking |
| 20 | MON87708 transgenic locus 3' Junction Polynucleotide |
| 21 | MON87708 transgenic locus 3' plant genomic flanking |
| 22 | INHT30-3 (gRNA-1 cut resulting in a deletion of 7 bp in a MON87708 5' junction polynucleotide sequence) |
| 23 | INHT30-4 (Insertion of 27 bp CgRRS with gRNA-1 cut and SEQ ID NO: 24 donor DNA template) |

TABLE 1-continued

Description of sequences.

| SEQ ID NO | Description |
|---|---|
| 24 | MON87708 CgRRS DNA donor template for generating INHT30-4 containing the SEQ ID NO: 8 CgRRS |
| 25 | INHT30-5 (gRNA-3 cut resulting in a deletion of 7 bp in a MON87708 5' junction polynucleotide sequence) |
| 26 | INHT30-6 (Insertion of 27 bp CgRRS with gRNA-3 cut and SEQ ID NO: 27 donor DNA template) |
| 27 | MON87708 CgRRS DNA donor template for generating INHT30-6 containing the SEQ ID NO: 10 CgRRS |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as soybean and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 1. In certain embodiments, INHT30 transgenic loci provided here are characterized by polynucleotide sequences that can facilitate as necessary the removal of the INHT30 transgenic loci from the genome. Useful applications of such INHT30 transgenic loci and related methods of making include targeted excision of a INHT30 transgenic locus or portion thereof in certain breeding lines to facilitate recovery of germplasm with subsets of transgenic traits tailored for specific geographic locations and/or grower preferences. Other useful applications of such INHT30 transgenic loci and related methods of making include removal of transgenic traits from certain breeding lines when it is desirable to replace the trait in the breeding line without disrupting other transgenic loci and/or non-transgenic loci. In certain embodiments, soybean genomes containing INHT30 transgenic loci or portions thereof which can be selectively excised with one or more gRNA molecules and RdDe (RNA dependent DNA endonucleases) which form gRNA/target DNA complexes. Such selectively excisable INHT30 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 2A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 3' junction polynucleotide in an MON87708 transgenic locus include SEQ ID NO: 7. OgRRS polynucleotide sequences located in a first junction polynucleotide can be introduced into the second junction polynucleotide using donor DNA templates as illustrated in FIG. 2A and as elsewhere described herein. A donor DNA template for introducing the SEQ ID NO: 7 OgRRS into the 5' junction polynucleotide of an MON87708 locus includes the donor DNA template of SEQ ID NO: 11 which comprises the SEQ ID NO: 9 CgRRS. Similar donor DNA templates comprising the SEQ ID NO: 8 or SEQ ID NO: 10 CgRRS elements and similar homology arms that target the MON87708 5' junction polynucleotide target sequence (e.g. SEQ ID NO; 12) can be used to obtain INHT20 transgenic loci comprising the SEQ ID NO: 8 or SEQ ID NO: 10 CgRRS elements. Double stranded breaks in a 5' junction polynucleotide of SEQ ID NO: 1 can be introduced with gRNAs encoded by SEQ ID NO: 4, 5, or 6 and a Cas12a nuclease. Integration of the SEQ ID NO: 11 donor DNA template into the 5' junction polynucleotide of an MON87708 locus at the double stranded breaks introduced by the gRNAs encoded by SEQ ID NO: 4, 5, or 6 and a Cas12a nuclease can provide an INHT30 locus comprising the CgRRS sequence set forth in SEQ ID NO: 9. Double stranded breaks in a 5' junction polynucleotide of SEQ ID NO: 1 can be introduced with gRNAs encoded by SEQ ID NO: 4, 5, or 6. Another donor DNA template adapted for insertion of the OgRRS of SEQ ID NO: 9 in a 5' junction polynucleotide of a MON87708 transgenic locus can comprise SEQ ID NO: 11. Double stranded breaks in a 5' junction polynucleotide of SEQ ID NO: 1 can be introduced with gRNAs encoded by SEQ ID NO: 5 and a Cas12a nuclease. A donor DNA template of SEQ ID NO: 11 or the equivalent thereof having longer or shorter homology arms can be used to obtain the CgRRS insertion in the 5' junction polynucleotide that is set forth in SEQ ID NO: 16. An INHT30-2 transgenic locus containing this CgRRS insertion is set forth in SEQ ID NO: 3. An INHT30-4 transgenic locus containing the CgRRS insertion of SEQ ID NO: 8 is set forth in SEQ ID NO: 23. The INHT30-4 transgenic locus of SEQ ID NO: 23 can be obtained by using gRNA-1 (SEQ ID NO: 4) with a Cas12A nuclease and the donor DNA template of SEQ ID NO: 24. An INHT30-6 transgenic locus containing the CgRRS insertion of SEQ ID NO: 10 is set forth in SEQ ID NO: 26. The INHT30-6 transgenic locus of SEQ ID NO: 26 can be obtained by using gRNA-3 (SEQ ID NO: 6) with a Cas12A nuclease and the donor DNA template of SEQ ID NO: 24.

Also provided are unique transgenic locus excision sites created by excision of INHT30 transgenic loci or selectively excisable INHT30 transgenic loci, DNA molecules comprising the INHT30 transgenic loci or unique fragments thereof (i. e., fragments of an INHT30 locus which are not found in an MON87708 transgenic locus), INHT30 plants comprising the same, biological samples containing the DNA, nucleic acid markers adapted for detecting the DNA molecules, and related methods of identifying soybean plants comprising unique INHT30 transgenic locus excision sites and unique fragments of a INHT30 transgenic locus. DNA molecules comprising unique fragments of an INHT30 transgenic locus are diagnostic for the presence of an INHT30 transgenic locus or fragments thereof in a soybean plant, soybean cell, soybean seed, products obtained therefrom (e.g., seed meal or stover), and biological samples. DNA molecules comprising unique fragments of an INHT30 transgenic locus include DNA molecules comprising Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the soybean MON87708 transgenic locus described in U.S. Pat. No. 9,447,428. Soybean plants comprising the MON87708 transgenic locus and seed thereof have been cultivated, been placed in commerce, and have been described in a variety of publications by various governmental bodies. Databases which have compiled descriptions of the MON87708 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the MON87708 transgenic locus which can be improved by the methods provided herein are set forth or otherwise provided in SEQ ID NO: 1, U.S. Pat. No. 9,447,428, the sequence of the MON87708 locus in the deposited seed of ATCC accession No. PTA-9670, and elsewhere in this disclosure. In certain embodiments provided herein, the MON87708 transgenic locus set forth in SEQ ID NO: 1 or present in the deposited seed of ATCC accession No. PTA-9670 is referred to as an "original MON87708 transgenic locus." Allelic or other variants of the sequence set forth SEQ ID NO: 1, the patent references set forth therein and incorporated herein by reference in their entireties, and elsewhere in this disclosure which may be present in certain variant MON87708 transgenic plant loci (e.g., progeny of deposited seed of accession No. PTA-9670 which contain allelic variants of SEQ ID NO:1 or progeny originating from transgenic plant cells comprising the original MON87708transgenic set forth in U.S. Pat. No. 9,447,428) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 10,579 nucleotides of SEQ ID NO: 1. Also provided are plants, plant parts including seeds, genomic DNA, and/or DNA obtained from INHT30 plants which comprise one or more modifications (e.g., via insertion of a CgRRS in a junction polynucleotide sequence) which provide for selective excision of the INHT30 transgenic locus or a portion thereof. Also provided herein are methods of detecting plants, genomic DNA, and/or DNA obtained from plants comprising a INHT30 transgenic locus which contains one or more of a CgRRS, deletions of selectable marker genes, deletions of non-essential DNA, and/or a transgenic locus excision site. A first junction polynucleotide of a MON87708 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INHT30 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the MON87708 transgenic locus of SEQ ID NO: 1, allelic variants thereof, or other variants thereof to obtain an INHT30 transgenic locus. In other embodiments, the OgRRS is found in non-transgenic DNA or transgenic DNA of the 3' junction polynucleotide of the MON87708 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INHT30 transgenic locus.

Also provided herein are allelic variants of any of the INHT30 transgenic loci or DNA molecules provided herein. In certain embodiments, such allelic variants of INHT30 transgenic loci include sequences having at least 85%, 90%, 95%, 98%, or 99% sequence identity across the entire length or at least 20, 40, 100, 500, 1,000, 2,000, 4,000, or nucleotides of SEQ ID NO: 2, 3, 22, 23, 25, and 26. In certain embodiments, such allelic variants of INHT30 DNA molecules include sequences having at least 85%, 90%, 95%, 98%, or 99% sequence identity across the entire length of SEQ ID NO: 3, 2, 8, 9, 10, 11, 16, 22, 23, 24, 25, 26, or 27.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INHT30 transgenic locus, in transgenic DNA of a DNA junction polynucleotide of an INHT30 transgenic locus or can span the junction of the transgenic and non-transgenic DNA of a DNA junction polynucleotide of an INHT30 transgenic locus. An OgRRS can likewise be located in non-transgenic plant genomic DNA of a DNA junction polynucleotide of an INHT30 transgenic locus, in transgenic DNA of a DNA junction polynucleotide of an INHT30 transgenic locus, or can span the junction of the transgenic and non-transgenic DNA of a DNA junction polynucleotide of an INHT30 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INHT30 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 1 (bottom "Alternative" panel), where two or more of the transgenic loci ("Event" in FIG. 1) are provided in Line A and then moved into elite crop plant germplasm by introgression. In the non-limiting FIG. 1 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 1) comprising two or more of the modified transgenic loci. This elite germplasm containing the modified transgenic loci (e.g., "Universal Donor" of FIG. 1) can then be subjected to genome editing molecules which can excise at least one of the transgenic loci ("Event Removal" in FIG. 1) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 1). In certain embodiments, it is also desirable to bulk up populations of inbred elite crop plants or their seed comprising the subset of transgenic loci and a transgenic locus excision site by selfing. In certain embodiments, inbred progeny of the selfed soybean plants comprising the INHT30 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INHT30 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INHT30 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INHT30 transgenic loci excision sites are provided herein.

In other embodiments, a segment comprising a INHT30 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 2C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MON87708 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INHT30 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the soybean plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ as depicted in FIG. 2B. In the depicted example set forth in FIG. 2B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a 1$^{st}$ junction polynucleotide and a 2$^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template. Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759,618, 7,157,281, 6,852,915, 7,705,216, 10,316,330, 8,618,358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INHT30 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 1, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target soybean genes that can be subjected to targeted gene edits to confer useful traits include: (a) ZmIPK1 (herbicide tolerant and phytate reduced soybean; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMSS (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including soybean which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature,* 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.,* 11:636-646; Mohanta et al. (2017) *Genes* vol. 8, 12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fokl, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 11 and equivalents thereof with longer or shorter homology arms. In certain embodiments, a donor DNA template can comprise an adapter molecule with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

Various treatments are useful in delivery of gene editing molecules and/or other molecules to a MON87708 or INHT30 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., Azobacter sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a MON87708 or INHT30 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferre-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from soybean, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a soybean chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the MON87708 or INHT30 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications,* 5:5334, doi: 10.1038/ncomms6334). Haploids can also be obtained in a wide variety of monocot plants (e.g., soybean, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing soybean lines that can be used to obtain haploid soybean plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MON87708 or INHT30 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MON87708 or INHT30 plant cells in used in the methods provided herein can include dividing cells. Dividing cells can include those cells found in various plant tissues including leaves, meristems, and embryos. These tissues include dividing cells from young soybean leaf, meristems and scutellar tissue from about 8 or 10 to about 12 or 14 days after pollination (DAP) embryos. The isolation of soybean embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a soybean plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INHT30 plant from a INHT30 plant cell that had been subjected to the gene editing or from a regenerable plant structure obtained from that INHT30 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INHT30 plant or its seeds, including: (a) soybean seed meal (defatted or non-defatted); (b) extracted proteins, oils, sugars, and starches; (c) fermentation products; (d) animal feed or human food products (e.g., feed and food comprising soybean seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (0 raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic soybean plant cell comprising an INHT30 transgenic locus comprising an originator guide RNA recognition site (OgRRS) in a first DNA junction polynucleotide of a MON87708 transgenic locus and a cognate guide RNA recognition site (CgRRS) in a second DNA junction polynucleotide of the MON87708 transgenic locus.

1b. A transgenic soybean plant cell comprising an INHT30 transgenic locus comprising an insertion and/or substitution of DNA in a DNA junction polynucleotide of a MON87708 transgenic locus with DNA comprising a cognate guide RNA recognition site (CgRRS) or a deletion in a 5' or 3' junction polynucleotide of a MON87708 transgenic locus.

2. The transgenic soybean plant cell of embodiment 1a or 1b, wherein said CgRRS comprises the DNA molecule set forth in SEQ ID NO: 9, 8, or 10; and/or wherein said MON87708 transgenic locus is set forth in SEQ ID NO:1, is present in seed deposited at the ATCC under accession No. PTA-9670, is present in progeny thereof, is present in allelic variants thereof, or is present in other variants thereof.

3. The transgenic soybean plant cell of embodiments 1a, 1b, or 2, wherein said INHT30 transgenic locus comprises the DNA molecule set forth in SEQ ID NO: 2, 3, 22, 23, 25, 26, or an allelic variant thereof.

4. A transgenic soybean plant part comprising the soybean plant cell of any one of embodiments 1a, 1b, 2, or 3, wherein said soybean plant part is optionally a seed.

5. A transgenic soybean plant comprising the soybean plant cell of any one of embodiments 1a, 1b, 2, or 3.

6. A method for obtaining a bulked population of inbred seed comprising selfing the transgenic soybean plant of embodiment 5 and harvesting seed comprising the INHT30 transgenic locus from the selfed soybean plant.

7. A method of obtaining hybrid soybean seed comprising crossing the transgenic soybean plant of embodiment 5 to a second soybean plant which is genetically distinct from the first soybean plant and harvesting seed comprising the INHT30 transgenic locus from the cross.

8. A DNA molecule comprising SEQ ID NO: 3, 2, 8, 9, 10, 11, 16, 22, 23, 24, 25, 26, 27, or an allelic variant thereof.

9. A processed transgenic soybean plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a soybean plant cell comprising the INHT30 transgenic locus of any one of embodiments 1a, 1b, 2, or 3, comprising the step of detecting DNA molecule comprising SEQ ID NO: 2, 3, 8, 9, 10, 11, 16, 22, 23, 24, 25, 26, 27, or an allelic variant thereof.

13. A method of excising the INHT30 transgenic locus from the genome of the soybean plant cell of any one of embodiments 1a, 1b, 2, or 3, comprising the steps of:

(a) contacting the INHT30 transgenic locus of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INHT30 transgenic locus flanked by the OgRRS and the CgRRS has been excised.

14. The method of embodiment 13, wherein said INHT30 transgenic locus comprises the CgRRS in SEQ ID NO:9, 8, or 10 and the guide RNA comprises an RNA sequence encoded by SEQ ID NO: 13.

15. The method of embodiment 14, wherein said INHT30 transgenic locus comprises the DNA molecule set forth in SEQ ID NO: 3, 23, 26, or an allelic variant thereof.

EXAMPLES

Example 1. Introduction of a CgRRS in a 5' Junction Polynucleotides of a MON87708 Transgenic Locus Transgenic plant genomes containing one or more of the following transgenic loci (events) are contacted with:
(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.
Plant cells, callus, parts, or whole plants comprising the introduced CgRRS in the transgenic plant genome are selected.

TABLE 2

Examples of OgRRS and CgRRS in MON87708

| EVENT NAME | OgRRS | CgRRS |
|---|---|---|
| MON87708 | (SEQ ID NO: 7; located in 3' junction polynucleotide of SEQ ID NO: 1) | (SEQ ID NO: 8; inserted into 5' junction polynucleotide) |
| | | (SEQ ID NO: 9; inserted into 5' junction polynucleotide) |
| | | (SEQ ID NO: 10; inserted into 5' junction polynucleotide) |

Example 2. Insertion of a CgRRS Element in the 5'-Junction of the MON87708 Event Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in their entireties. DNA sequences encoding the c2 NLS-Exo, c2 NLS lambda beta S SAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 11) that targets the 5'-T-DNA junction polynucleotide of the MON87708 event (SEQ ID NO:1) for HDR-mediated insertion of a base pair OgRRS sequence (SEQ ID NO: 7) that is identical to a Cas12a recognition site at the 5'-junction polynucleotide of the MON87708 T-DNA insert is constructed. The DNA donor sequence includes a replacement template with desired insertion region (27 base pairs long) flanked on both sides by homology arms about 550 bp in length. The homology arms match (i.e., are homologous to) gDNA (genomic DNA) regions flanking the target gDNA insertion site (SEQ ID NO: 9). The replacement template region comprising the donor DNA is flanked at each end by DNA sequences identical to the MON87708 5'-T-DNA junction polynucleotide sequence recognized by a Cas12a RNA-guided nuclease and a gRNA (e.g., encoded by SEQ ID NO: 9).

A plant expression cassette that provides for expression of the RNA-guided sequence-specific Cas12a endonuclease is constructed. A plant expression cassette that provides for expression of a guide RNA (e.g., encoded by SEQ ID NO: 9) complementary to sequences adjacent to the insertion site is constructed. An *Agrobacterium* superbinary plasmid transformation vector containing a cassette that provides for the expression of the phosphinothricin N-acetyltransferasesynthase (PAT) protein is constructed. Once the cassettes, donor sequence and *Agrobacterium* superbinary plasmid transformation vector are constructed, they are combined to generate two soybean transformation plasmids.

A soybean transformation plasmid is constructed with the PAT cassette, the RNA-guided sequence-specific endonuclease cassette, the guide RNA cassette, and the MON87708 5'-T_DNA junction sequence DNA donor sequence into the *Agrobacterium* superbinary plasmid transformation vector (the control vector).

A soybean transformation plasmid is constructed with the PAT cassette, the RNA-guided sequence-specific endonuclease cassette, the guide RNA cassette, the SSB cassette, the lambda beta SSAP cassette, the Exo cassette, and the MON87708 5'-T_DNA junction sequence donor DNA template sequence (e.g., SEQ ID NO: 11) into the *Agrobacterium* superbinary plasmid transformation vector (the lambda red vector).

All constructs are transformed into *Agrobacterium* strain LBA4404.

Soybean transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination.

Embryos are placed in an *Agrobacterium* suspension made with infection medium at a concentration of OD 600=1.0. Acetosyringone (200 μM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remained on Pre-Regeneration media for 7 days. Calli beginning to initiate shoots are transferred to Regeneration medium with 7.5 mg/L PPT in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the MON87708 junction sequence, using a PCR-based approach. The PCR primer on the 5'-end is 5'-3' (SEQ ID NO: 14). The PCR primer on the 3'-end is 5'-3' (SEQ ID NO: 15). The above primers that flank donor DNA homology arms are used to amplify the MON87708 5'-junction polynucleotide sequence. The correct donor sequence insertion will produce a 1375 bp product. A unique DNA fragment comprising the CgRRS in the MON87708 5' junction polynucleotide is set forth in SEQ ID NO: 16. Amplicons can be sequenced directly using an amplicon sequencing approach or ligated to a convenient plasmid vector for Sanger sequencing. Those plants in which the MON87708 junction sequence now contains the intended Cas12a recognition sequence are selected and grown to maturity. The T-DNA encoding the Cas12a reagents can be segregated away from the modified junction sequence in a subsequent generation. The resultant INHT30 transgenic locus (SEQ ID NO: 3) comprising the CgRRS and OgRRS (e.g., which each comprise SEQ ID NO: 7) can be excised using Cas12a and a suitable gRNA which hybridizes to DNA comprising SEQ ID NO: 13 at both the OgRRS and the CgRRS.

The breadth and scope of the present disclosure should not be limited by any of the above-described embodiments.

What is claimed is:

1. A transgenic soybean plant cell comprising an INHT30 transgenic locus comprising the DNA molecule set forth in SEQ ID NO: 23.

2. A transgenic soybean plant part comprising the soybean plant cell of claim 1.

3. The transgenic soybean plant part of claim 2, wherein said soybean plant part is a seed.

4. A transgenic soybean plant comprising the soybean plant cell of claim 1.

5. A method for obtaining a bulked population of inbred seed comprising selfing the transgenic soybean plant of claim 4 and harvesting seed comprising the INHT30 transgenic locus from the selfed soybean plant.

6. A method of obtaining hybrid soybean seed comprising crossing the transgenic soybean plant of claim 4 to a second soybean plant which is genetically distinct from the first soybean plant and harvesting seed comprising the INHT30 transgenic locus from the cross.

7. A DNA molecule comprising SEQ ID NO: 23.

8. A processed transgenic soybean plant product comprising the DNA molecule of claim 7.

9. A biological sample containing the DNA molecule of claim 7.

10. A method of detecting a soybean plant cell comprising the INHT30 transgenic locus of claim 1, comprising the step of detecting DNA molecule comprising SEQ ID NO: 8.

11. A method of excising the INHT30 transgenic locus from the genome of the soybean plant cell of claim 1, comprising the steps of: (a) contacting the INHT30 transgenic locus of the plant cell with: (i) a Cas12a RNA dependent DNA endonuclease (RdDe); and (ii) a guide RNA (gRNA) capable of hybridizing to the guide RNA hybridization site of the originator guide RNA recognition site (OgRRS) and the cognate guide RNA recognition site (CgRRS) of SEQ ID NO: 23; wherein the Cas12a RdDe recognizes a OgRRS/gRNA and a CgRRS/gRNA hybridization complex; and, (b) selecting a transgenic plant cell, transgenic plant part, or transgenic plant wherein the INHT30 transgenic locus flanked by the OgRRS and the CgRRS has been excised.

12. The method of claim 11, wherein said guide RNA comprises an RNA sequence encoded by SEQ ID NO: 13.

* * * * *